United States Patent
Atiya et al.

(10) Patent No.: US 11,369,271 B2
(45) Date of Patent: *Jun. 28, 2022

(54) APPARATUS FOR DENTAL IMAGING

(71) Applicant: Align Technology, Inc., San Jose, CA (US)

(72) Inventors: Yossef Atiya, Maccabim (IL); Tal Verker, Ofra (IL); Nir Makmel, Tel Aviv (IL)

(73) Assignee: Align Technology, Inc., San Jose, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 17/037,398

(22) Filed: Sep. 29, 2020

(65) Prior Publication Data

US 2021/0022611 A1    Jan. 28, 2021

Related U.S. Application Data

(63) Continuation of application No. 16/820,505, filed on Mar. 16, 2020, now Pat. No. 10,835,128, which is a
(Continued)

(51) Int. Cl.
*A61B 5/00* (2006.01)
*G02B 13/16* (2006.01)
(Continued)

(52) U.S. Cl.
CPC .......... *A61B 5/0088* (2013.01); *A61C 9/0066* (2013.01); *G01B 11/24* (2013.01);
(Continued)

(58) Field of Classification Search
CPC ..... A61B 5/0088; A61C 9/0066; G01B 11/24; G01B 11/245; G02B 13/16; G02B 6/0006; G02B 6/262
See application file for complete search history.

(56) References Cited

U.S. PATENT DOCUMENTS 2,171,695 A    9/1939  Harper
2,467,432 A    4/1949  Kesling
(Continued)

FOREIGN PATENT DOCUMENTS

AU    3031677 A    5/1979
AU    3031677 B    7/1981
(Continued)

OTHER PUBLICATIONS

Sirona Dental Systems GmbH, CEREC 3D, Manuel Utiiisateur, Version 2.0X (in French), 2003, 114 pages total.
(Continued)

*Primary Examiner* — Shawn Decenzo
*Assistant Examiner* — Jarreas C. Underwood
(74) *Attorney, Agent, or Firm* — Lowenstein Sandler LLP

(57) ABSTRACT

An apparatus for dental imaging comprises a light source for generating light, an optics system for focusing the light, and a light-guiding part having an entrance face and an exit face. The light source, the optics system and the light-guiding part are arranged such that the light passes through the optics system, enters the light-guiding part via the entrance face, and exits the light-guiding part via the exit face. The optics system is configured such that, upon entering the light-guiding part, an outermost chief ray of the light with respect to an optical axis of the optics system is divergent to the optical axis and an outermost marginal ray of the light with respect to the optical axis is parallel or divergent to the optical axis.

20 Claims, 3 Drawing Sheets

Related U.S. Application Data continuation of application No. 14/741,172, filed on Jun. 16, 2015, now Pat. No. 10,772,506.

(60) Provisional application No. 62/021,608, filed on Jul. 7, 2014.

(51) Int. Cl.

| | | |
|---|---|---|
| *G02B 6/26* | (2006.01) | |
| *G01B 11/24* | (2006.01) | |
| *G01B 11/245* | (2006.01) | |
| *G02B 5/04* | (2006.01) | |
| *G02B 23/24* | (2006.01) | |
| *G02B 6/00* | (2006.01) | |
| *F21V 8/00* | (2006.01) | |
| *A61C 9/00* | (2006.01) | |

(52) U.S. Cl.
CPC ............ *G01B 11/245* (2013.01); *G02B 5/04* (2013.01); *G02B 6/0006* (2013.01); *G02B 6/0046* (2013.01); *G02B 6/262* (2013.01); *G02B 13/16* (2013.01); *G02B 23/2461* (2013.01); *G01B 2210/50* (2013.01); *G02B 2006/0098* (2013.01)

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,255,138 A | 3/1981 | Frohn |
| 4,324,546 A | 4/1982 | Heitlinger et al. |
| 4,324,547 A | 4/1982 | Arcan et al. |
| 4,348,177 A | 9/1982 | Kurz |
| 4,348,178 A | 9/1982 | Kurz |
| 4,419,992 A | 12/1983 | Chorbajian |
| 4,433,956 A | 2/1984 | Witzig |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,519,386 A | 5/1985 | Sullivan |
| 4,526,540 A | 7/1985 | Dellinger |
| 4,575,330 A | 3/1986 | Hull |
| 4,575,805 A * | 3/1986 | Moermann ........ G05B 19/4207 433/55 |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 10/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 6/1991 | Breads et al. |
| 5,037,295 A | 8/1991 | Bergersen |
| 5,055,039 A | 10/1991 | Abbatte et al. |
| 5,059,118 A | 10/1991 | Breads et al. |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon, Jr. et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,204,670 A | 4/1993 | Stinton |
| 5,242,304 A | 4/1993 | Truax et al. |
| 5,245,592 A | 9/1993 | Kuemmel et al. |
| 5,257,203 A | 10/1993 | Riley et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry, Jr. et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A * | 12/1994 | Massen .................. A61B 1/24 433/215 |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 9/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,499,633 A | 3/1996 | Fenton |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,543,780 A | 8/1996 | McAuley et al. |
| 5,549,476 A | 8/1996 | Stern |

(56) References Cited

U.S. PATENT DOCUMENTS

| | | | |
|---|---|---|---|
| 5,562,448 A | 10/1996 | Mushabac | |
| 5,570,182 A | 10/1996 | Nathel et al. | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre, Sr. | |
| 5,621,648 A | 4/1997 | Crump | |
| 5,626,537 A | 5/1997 | Danyo et al. | |
| 5,645,420 A | 7/1997 | Bergersen | |
| 5,645,421 A | 7/1997 | Slootsky | |
| 5,651,671 A | 7/1997 | Seay et al. | |
| 5,655,653 A | 8/1997 | Chester | |
| 5,659,420 A | 8/1997 | Wakai et al. | |
| 5,683,243 A | 11/1997 | Andreiko et al. | |
| 5,683,244 A | 11/1997 | Truax | |
| 5,691,539 A | 11/1997 | Pfeiffer | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,737,084 A | 4/1998 | Ishihara | |
| 5,740,267 A | 4/1998 | Echerer et al. | |
| 5,742,700 A | 4/1998 | Yoon et al. | |
| 5,769,631 A | 6/1998 | Williams | |
| 5,774,425 A | 6/1998 | Ivanov et al. | |
| 5,790,242 A | 8/1998 | Stern et al. | |
| 5,799,100 A | 8/1998 | Clarke et al. | |
| 5,800,174 A | 9/1998 | Andersson | |
| 5,816,800 A | 10/1998 | Brehm et al. | |
| 5,818,587 A | 10/1998 | Devaraj et al. | |
| 5,823,778 A | 10/1998 | Schmitt et al. | |
| 5,848,115 A | 12/1998 | Little et al. | |
| 5,857,853 A | 1/1999 | van Nifterick et al. | |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,904,479 A | 5/1999 | Staples | |
| 5,934,288 A | 8/1999 | Avila et al. | |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 5,980,246 A | 11/1999 | Ramsay et al. | |
| 5,989,023 A | 11/1999 | Summer et al. | |
| 6,015,289 A | 1/2000 | Andreiko et al. | |
| 6,044,309 A | 3/2000 | Honda | |
| 6,049,743 A | 4/2000 | Baba | |
| 6,053,731 A | 4/2000 | Heckenberger | |
| 6,062,861 A | 5/2000 | Andersson | |
| 6,068,482 A | 5/2000 | Snow | |
| 6,099,303 A | 8/2000 | Gibbs et al. | |
| 6,099,314 A | 8/2000 | Kopelman et al. | |
| 6,123,544 A | 9/2000 | Cleary | |
| 6,152,731 A | 11/2000 | Jordan et al. | |
| 6,154,676 A | 11/2000 | Levine | |
| 6,183,248 B1 | 2/2001 | Chishti et al. | |
| 6,186,780 B1 | 2/2001 | Hibst et al. | |
| 6,190,165 B1 | 2/2001 | Andreiko et al. | |
| 6,200,133 B1 | 3/2001 | Kittelsen | |
| 6,201,880 B1 | 3/2001 | Elbaum et al. | |
| 6,212,435 B1 | 4/2001 | Lattner et al. | |
| 6,217,325 B1 | 4/2001 | Chishti et al. | |
| 6,217,334 B1 | 4/2001 | Hultgren | |
| 6,231,338 B1 | 5/2001 | de Josselin de Jong et al. | |
| 6,239,705 B1 | 5/2001 | Glen | |
| 6,243,601 B1 | 6/2001 | Wist | |
| 6,244,861 B1 | 6/2001 | Andreiko et al. | |
| 6,248,988 B1 | 6/2001 | Krantz | |
| 6,263,234 B1 * | 7/2001 | Engelhardt | A61B 5/0088 |
| | | | 250/559.22 |
| 6,299,438 B1 | 10/2001 | Sahagian et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,328,745 B1 | 12/2001 | Ascherman | |
| 6,334,073 B1 | 12/2001 | Levine | |
| 6,350,120 B1 | 2/2002 | Sachdeva et al. | |
| 6,364,660 B1 | 4/2002 | Durbin et al. | |
| 6,382,975 B1 | 5/2002 | Poirier | |
| 6,398,548 B1 | 6/2002 | Muhammad et al. | |
| 6,402,510 B1 | 6/2002 | Williams | |
| 6,402,707 B1 | 6/2002 | Ernst | |
| 6,405,729 B1 | 6/2002 | Thornton | |
| 6,436,058 B1 | 8/2002 | Krahner et al. | |
| 6,450,807 B1 | 9/2002 | Chishti et al. | |
| 6,482,298 B1 | 11/2002 | Bhatnagar | |
| 6,499,995 B1 | 12/2002 | Schwartz | |
| 6,515,593 B1 | 2/2003 | Stark et al. | |
| 6,516,805 B1 | 2/2003 | Thornton | |
| 6,520,772 B2 | 2/2003 | Williams | |
| 6,524,101 B1 | 2/2003 | Phan et al. | |
| 6,540,707 B1 | 4/2003 | Stark et al. | |
| 6,554,611 B2 | 4/2003 | Chishti et al. | |
| 6,572,372 B1 | 6/2003 | Phan et al. | |
| 6,573,998 B2 | 6/2003 | Cohen-Sabban | |
| 6,594,539 B1 * | 7/2003 | Geng | A61B 1/0646 |
| | | | 264/16 |
| 6,597,934 B1 | 7/2003 | de Jong et al. | |
| 6,602,070 B2 | 8/2003 | Miller et al. | |
| 6,611,783 B2 | 8/2003 | Kelly, Jr. et al. | |
| 6,613,001 B1 | 9/2003 | Dworkin | |
| 6,616,579 B1 | 9/2003 | Reinbold et al. | |
| 6,623,698 B2 | 9/2003 | Kuo | |
| 6,624,752 B2 | 9/2003 | Klitsgaard et al. | |
| 6,626,180 B1 | 9/2003 | Kittelsen et al. | |
| 6,629,840 B2 | 10/2003 | Chishti et al. | |
| 6,640,128 B2 | 10/2003 | Vilsmeier et al. | |
| 6,697,164 B1 * | 2/2004 | Babayoff | A61B 5/0088 |
| | | | 356/601 |
| 6,702,765 B2 | 3/2004 | Robbins et al. | |
| 6,702,804 B1 | 3/2004 | Ritter et al. | |
| 6,705,863 B2 | 3/2004 | Phan et al. | |
| 6,722,880 B2 | 4/2004 | Chishti et al. | |
| 6,830,450 B2 | 12/2004 | Knopp et al. | |
| 6,885,464 B1 | 4/2005 | Pfeiffer et al. | |
| 6,890,285 B2 | 5/2005 | Rahman et al. | |
| 6,940,611 B2 | 9/2005 | Babayoff et al. | |
| 7,036,514 B2 | 5/2006 | Heck | |
| 7,092,107 B2 | 8/2006 | Babayoff et al. | |
| 7,106,233 B2 | 9/2006 | Schroeder et al. | |
| 7,112,065 B2 | 9/2006 | Kopelman et al. | |
| 7,121,825 B2 | 10/2006 | Chishti et al. | |
| 7,138,640 B1 * | 11/2006 | Delgado | G02B 27/0006 |
| | | | 250/372 |
| 7,142,312 B2 | 11/2006 | Quadling et al. | |
| 7,166,063 B2 | 1/2007 | Rahman et al. | |
| 7,184,150 B2 | 2/2007 | Quadling et al. | |
| 7,192,273 B2 | 3/2007 | McSurdy, Jr. | |
| 7,220,124 B2 | 5/2007 | Taub et al. | |
| 7,230,725 B2 | 6/2007 | Babayoff et al. | |
| 7,286,954 B2 | 10/2007 | Kopelman et al. | |
| 7,292,759 B2 | 11/2007 | Boutoussov et al. | |
| 7,302,842 B2 | 12/2007 | Biester et al. | |
| 7,338,327 B2 | 3/2008 | Sticker et al. | |
| D565,509 S | 4/2008 | Fechner et al. | |
| 7,351,116 B2 | 4/2008 | Dold | |
| 7,357,637 B2 | 4/2008 | Liechtung | |
| 7,450,231 B2 | 11/2008 | Johs et al. | |
| 7,458,810 B2 | 12/2008 | Bergersen | |
| 7,460,230 B2 | 12/2008 | Johs et al. | |
| 7,462,076 B2 | 12/2008 | Walter et al. | |
| 7,463,929 B2 | 12/2008 | Simmons | |
| 7,477,402 B2 | 1/2009 | Babayoff et al. | |
| 7,488,174 B2 | 2/2009 | Kopelman et al. | |
| 7,500,851 B2 | 3/2009 | Williams | |
| D594,413 S | 6/2009 | Palka et al. | |
| 7,544,103 B2 | 6/2009 | Walter et al. | |
| 7,553,157 B2 | 6/2009 | Abolfathi et al. | |
| 7,561,273 B2 | 7/2009 | Stautmeister et al. | |
| 7,577,284 B2 | 8/2009 | Wong et al. | |
| 7,596,253 B2 | 9/2009 | Wong et al. | |
| 7,597,594 B2 | 10/2009 | Stadler et al. | |
| 7,609,875 B2 | 10/2009 | Liu et al. | |

(56) References Cited

U.S. PATENT DOCUMENTS

| | | |
|---|---|---|
| D603,796 S | 11/2009 | Sticker et al. |
| 7,616,319 B1 | 11/2009 | Woollam et al. |
| 7,626,705 B2 | 12/2009 | Altendorf |
| 7,630,089 B2 | 12/2009 | Babayoff et al. |
| 7,632,216 B2 | 12/2009 | Rahman et al. |
| 7,633,625 B1 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Muller |
| 7,695,327 B2 | 4/2010 | Bauerle et al. |
| 7,698,068 B2 | 4/2010 | Babayoff |
| 7,724,378 B2 | 5/2010 | Babayoff |
| D618,619 S | 6/2010 | Walter |
| 7,731,508 B2 | 6/2010 | Borst |
| 7,735,217 B2 | 6/2010 | Borst |
| 7,780,460 B2 | 8/2010 | Walter |
| 7,787,132 B2 | 8/2010 | Korner et al. |
| 7,791,810 B2 | 9/2010 | Powell |
| 7,796,243 B2 | 9/2010 | Choo-Smith et al. |
| 7,796,277 B2 | 9/2010 | Babayoff et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 * | 1/2011 | Ertl ................... G01N 21/49 356/497 |
| 7,874,836 B2 | 1/2011 | McSurdy, Jr. |
| 7,874,849 B2 | 1/2011 | Sticker et al. |
| 7,878,801 B2 | 2/2011 | Abolfathi et al. |
| 7,907,280 B2 | 3/2011 | Johs et al. |
| 7,929,151 B2 | 4/2011 | Liang et al. |
| 7,942,671 B2 | 5/2011 | Taub et al. |
| 7,944,569 B2 | 5/2011 | Babayoff et al. |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 7,990,548 B2 | 8/2011 | Babayoff et al. |
| 8,017,891 B2 | 9/2011 | Nevin |
| 8,026,916 B2 | 9/2011 | Wen |
| 8,027,709 B2 | 9/2011 | Arnone et al. |
| 8,054,556 B2 * | 11/2011 | Chen ................... G02B 17/08 359/728 |
| 8,077,949 B2 | 12/2011 | Liang et al. |
| 8,083,556 B2 | 12/2011 | Stadler et al. |
| D652,799 S | 1/2012 | Mueller |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 * | 10/2012 | Oota ................... A61B 1/24 433/29 |
| 8,292,617 B2 | 10/2012 | Brandt et al. |
| 8,294,657 B2 | 10/2012 | Kim et al. |
| 8,297,286 B2 | 10/2012 | Smernoff |
| 8,306,608 B2 | 11/2012 | Mandelis et al. |
| 8,310,683 B2 | 11/2012 | Babayoff et al. |
| 8,314,764 B2 | 11/2012 | Kim et al. |
| 8,332,015 B2 | 12/2012 | Ertl |
| 8,354,588 B2 | 1/2013 | Sticker et al. |
| 8,363,228 B2 | 1/2013 | Babayoff |
| 8,366,479 B2 | 2/2013 | Borst et al. |
| 8,451,456 B2 | 5/2013 | Babayoff |
| 8,454,364 B2 | 6/2013 | Taub et al. |
| 8,465,280 B2 | 6/2013 | Sachdeva et al. |
| 8,477,320 B2 | 7/2013 | Stock et al. |
| 8,488,113 B2 * | 7/2013 | Thiel ................... G01J 3/02 356/73 |
| 8,520,922 B2 | 8/2013 | Wang et al. |
| 8,520,925 B2 | 8/2013 | Duret |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,594,408 B2 * | 11/2013 | Alpern ................... A61B 6/032 382/154 |
| 8,638,447 B2 | 1/2014 | Babayoff et al. |
| 8,638,448 B2 | 1/2014 | Babayoff et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,870,566 B2 | 10/2014 | Bergersen |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rosch |
| 8,992,216 B2 | 3/2015 | Karazivan |
| 9,022,792 B2 | 5/2015 | Sticker et al. |
| 9,039,418 B1 | 5/2015 | Rubber |
| 9,084,535 B2 | 7/2015 | Girkin et al. |
| 9,089,277 B2 | 7/2015 | Babayoff et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,242,118 B2 | 1/2016 | Brawn |
| 9,261,358 B2 * | 2/2016 | Atiya ................... A61B 1/04 |
| 9,299,192 B2 | 3/2016 | Kopelman |
| 9,336,336 B2 | 5/2016 | Deichmann et al. |
| 9,408,743 B1 | 8/2016 | Wagner |
| 9,433,476 B2 | 9/2016 | Khardekar et al. |
| 9,439,568 B2 | 9/2016 | Atiya et al. |
| 9,444,981 B2 * | 9/2016 | Bellis ................... H04N 5/2251 |
| 9,500,635 B2 | 11/2016 | Islam |
| 9,506,808 B2 | 11/2016 | Jeon et al. |
| 9,513,470 B1 * | 12/2016 | Weaver ................ G02B 21/008 |
| 9,545,331 B2 | 1/2017 | Ingemarsson-Matzen |
| 9,584,771 B2 | 2/2017 | Mandelis et al. |
| 9,675,430 B2 | 6/2017 | Verker et al. |
| 9,693,839 B2 | 7/2017 | Atiya et al. |
| 9,744,006 B2 | 8/2017 | Ross |
| 9,936,186 B2 | 4/2018 | Jesenko et al. |
| 10,307,222 B2 | 6/2019 | Morton et al. |
| 10,537,406 B2 | 1/2020 | Wu et al. |
| 10,772,506 B2 * | 9/2020 | Atiya ................... G02B 5/04 |
| 10,835,128 B2 * | 11/2020 | Atiya ................... G02B 6/0046 |
| 11,202,574 B2 * | 12/2021 | Atiya ................... A61C 9/0066 |
| 2001/0038705 A1 | 11/2001 | Rubbert et al. |
| 2002/0006597 A1 | 1/2002 | Andreiko et al. |
| 2002/0010568 A1 | 1/2002 | Rubbert et al. |
| 2002/0015934 A1 | 2/2002 | Rubbert et al. |
| 2003/0009252 A1 | 1/2003 | Pavlovskaia et al. |
| 2003/0048540 A1 * | 3/2003 | Xie ................... G02B 21/0056 359/637 |
| 2003/0139834 A1 | 7/2003 | Nikolskiy et al. |
| 2003/0190575 A1 | 10/2003 | Hilliard |
| 2003/0207224 A1 | 11/2003 | Lotte |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0058295 A1 | 3/2004 | Bergersen |
| 2004/0080754 A1 | 4/2004 | Tobiason et al. |
| 2004/0090638 A1 | 5/2004 | Babayoff et al. |
| 2004/0094165 A1 | 5/2004 | Cook |
| 2004/0128010 A1 | 7/2004 | Pavlovskaia et al. |
| 2005/0031196 A1 | 2/2005 | Moghaddam et al. |
| 2005/0037312 A1 | 2/2005 | Uchida |
| 2005/0048433 A1 | 3/2005 | Hilliard |
| 2005/0055118 A1 | 3/2005 | Nikolskiy et al. |
| 2005/0080503 A1 | 4/2005 | Kopelman et al. |
| 2005/0100333 A1 * | 5/2005 | Kerschbaumer ...... A61B 1/0676 396/16 |

(56) References Cited

U.S. PATENT DOCUMENTS

| | | |
|---|---|---|
| 2005/0181333 A1 | 8/2005 | Karazivan et al. |
| 2005/0186524 A1 | 8/2005 | Abolfathi et al. |
| 2005/0244781 A1 | 11/2005 | Abels et al. |
| 2005/0250075 A1 | 11/2005 | Taub et al. |
| 2005/0264828 A1 | 12/2005 | Babayoff et al. |
| 2005/0283065 A1 | 12/2005 | Babayoff |
| 2006/0001739 A1 | 1/2006 | Babayoff |
| 2006/0029523 A1 | 2/2006 | Tanaami |
| 2006/0084024 A1 | 4/2006 | Farrell |
| 2006/0087658 A1 | 4/2006 | Sesko et al. |
| 2006/0099546 A1 | 5/2006 | Bergersen |
| 2006/0154198 A1 | 7/2006 | Durbin et al. |
| 2006/0158665 A1 | 7/2006 | Babayoff et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0275737 A1 | 12/2006 | Kopelman et al. |
| 2007/0046865 A1 | 3/2007 | Umeda et al. |
| 2007/0053048 A1 | 3/2007 | Kumar et al. |
| 2007/0077537 A1 | 4/2007 | Taub et al. |
| 2007/0087300 A1 | 4/2007 | Willison et al. |
| 2007/0109559 A1 | 5/2007 | Babayoff et al. |
| 2007/0154867 A1 | 7/2007 | Taub et al. |
| 2007/0184402 A1 | 8/2007 | Boutoussov et al. |
| 2007/0231765 A1 | 10/2007 | Phan et al. |
| 2007/0253059 A1 | 11/2007 | Johs et al. |
| 2007/0296959 A1 | 12/2007 | Schwotzer |
| 2008/0045053 A1 | 2/2008 | Stadler et al. |
| 2008/0062429 A1 | 3/2008 | Liang et al. |
| 2008/0063998 A1 | 3/2008 | Liang et al. |
| 2008/0090208 A1 | 4/2008 | Rubbert |
| 2008/0100842 A1 | 5/2008 | Johs et al. |
| 2008/0115791 A1 | 5/2008 | Heine |
| 2008/0176448 A1 | 7/2008 | Muller et al. |
| 2008/0242144 A1 | 10/2008 | Dietz |
| 2009/0030347 A1 | 1/2009 | Cao |
| 2009/0040740 A1 | 2/2009 | Muller et al. |
| 2009/0053879 A1 | 2/2009 | Sim |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0091758 A1 | 4/2009 | Johs et al. |
| 2009/0148807 A1 | 6/2009 | Babayoff et al. |
| 2009/0153879 A1 | 6/2009 | Babayoff et al. |
| 2009/0210032 A1 | 8/2009 | Beiski et al. |
| 2009/0218514 A1 | 9/2009 | Klunder et al. |
| 2009/0298017 A1 | 12/2009 | Boerjes et al. |
| 2009/0305540 A1 | 12/2009 | Stadler et al. |
| 2010/0045902 A1 | 2/2010 | Ikeda et al. |
| 2010/0085636 A1 | 4/2010 | Berner |
| 2010/0099984 A1 | 4/2010 | Graser |
| 2010/0152599 A1 | 6/2010 | DuHamel et al. |
| 2010/0165275 A1 | 7/2010 | Tsukamoto et al. |
| 2010/0165357 A1 | 7/2010 | Babayoff et al. |
| 2010/0165358 A1 | 7/2010 | Babayoff et al. |
| 2010/0167225 A1 | 7/2010 | Kuo |
| 2010/0202034 A1 | 8/2010 | Freeman et al. |
| 2010/0231577 A1 | 9/2010 | Kim et al. |
| 2010/0312484 A1 | 12/2010 | DuHamel et al. |
| 2011/0045428 A1 | 2/2011 | Boltunov et al. |
| 2011/0081625 A1 | 4/2011 | Fuh |
| 2011/0102549 A1 | 5/2011 | Takahashi |
| 2011/0102566 A1 | 5/2011 | Zakian et al. |
| 2011/0143673 A1 | 6/2011 | Landesman et al. |
| 2011/0183294 A1 | 7/2011 | Taub et al. |
| 2011/0229840 A1 | 9/2011 | Liang et al. |
| 2011/0235045 A1 | 9/2011 | Koerner et al. |
| 2011/0269092 A1 | 11/2011 | Kuo et al. |
| 2012/0081786 A1 | 4/2012 | Mizuyama et al. |
| 2012/0086681 A1 | 4/2012 | Kim et al. |
| 2012/0092461 A1 | 4/2012 | Fisker et al. |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0089828 A1 | 4/2013 | Borovinskih et al. |
| 2013/0094031 A1 | 4/2013 | Babayoff et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0177866 A1 | 7/2013 | Babayoff et al. |
| 2013/0201488 A1 | 8/2013 | Ishihara |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0275107 A1* | 10/2013 | Alpern ............. A61C 9/0046 382/128 |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2014/0022352 A1 | 1/2014 | Fisker et al. |
| 2014/0081091 A1 | 3/2014 | Abolfathi et al. |
| 2014/0104620 A1 | 4/2014 | Babayoff et al. |
| 2014/0272774 A1 | 9/2014 | Dillon et al. |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0363778 A1 | 12/2014 | Parker |
| 2015/0002649 A1 | 1/2015 | Nowak et al. |
| 2015/0029309 A1 | 1/2015 | Michaeli et al. |
| 2015/0079531 A1 | 3/2015 | Heine |
| 2015/0140502 A1 | 5/2015 | Brawn et al. |
| 2015/0164335 A1 | 6/2015 | Van Der Poel et al. |
| 2015/0173856 A1 | 6/2015 | Lowe et al. |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0247950 A1 | 9/2015 | Perkins |
| 2015/0306486 A1 | 10/2015 | Logan et al. |
| 2015/0320320 A1 | 11/2015 | Kopelman et al. |
| 2015/0325044 A1 | 11/2015 | Lebovitz |
| 2015/0338209 A1 | 11/2015 | Knuttel |
| 2015/0348320 A1 | 12/2015 | Pesach et al. |
| 2016/0000332 A1* | 1/2016 | Atiya ................ G02B 6/0046 433/29 |
| 2016/0003610 A1 | 1/2016 | Lampert et al. |
| 2016/0015489 A1 | 1/2016 | Atiya et al. |
| 2016/0022389 A1 | 1/2016 | Esbech et al. |
| 2016/0045291 A1 | 2/2016 | Verker et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0296303 A1 | 10/2016 | Parker |
| 2016/0328843 A1 | 11/2016 | Graham et al. |
| 2016/0330355 A1 | 11/2016 | Tchouprakov et al. |
| 2017/0007366 A1 | 1/2017 | Kopelman et al. |
| 2017/0007367 A1 | 1/2017 | Li et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0156821 A1 | 6/2017 | Kopelman et al. |
| 2017/0265970 A1 | 9/2017 | Verker et al. |
| 2017/0325690 A1 | 11/2017 | Salah et al. |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0125610 A1 | 5/2018 | Carrier, Jr. et al. |
| 2018/0153648 A1 | 6/2018 | Shanjani et al. |
| 2018/0153649 A1 | 6/2018 | Wu et al. |

(56) References Cited

U.S. PATENT DOCUMENTS

| | | |
|---|---|---|
| 2018/0153733 A1 | 6/2018 | Kuo |
| 2018/0280118 A1 | 10/2018 | Cramer |
| 2018/0284727 A1 | 10/2018 | Cramer et al. |
| 2019/0105130 A1 | 4/2019 | Grove et al. |

FOREIGN PATENT DOCUMENTS

| | | |
|---|---|---|
| AU | 9150082 A | 6/1984 |
| AU | 5598894 A | 6/1994 |
| CA | 1121955 A1 | 4/1982 |
| DE | 2749802 A1 | 5/1978 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0091876 A1 | 10/1983 |
| EP | 0299490 A2 | 1/1989 |
| EP | 0376873 A2 | 7/1990 |
| EP | 0428152 A1 | 5/1991 |
| EP | 490848 A2 | 6/1992 |
| EP | 541500 A1 | 5/1993 |
| EP | 0667753 B1 | 8/1995 |
| EP | 0714632 B1 | 5/1997 |
| EP | 774933 B1 | 12/2000 |
| EP | 731673 B1 | 5/2001 |
| EP | 1941843 A2 | 7/2008 |
| EP | 2213223 A1 | 8/2010 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2652256 A1 | 3/1991 |
| FR | 2930334 A1 | 10/2009 |
| GB | 1550777 A | 8/1979 |
| JP | H53-058191 A | 5/1978 |
| JP | 04-028359 A | 1/1992 |
| JP | H08-508174 A | 9/1996 |
| JP | 63-11148 | 1/1998 |
| JP | 2002-522752 A | 7/2002 |
| JP | 2007-260158 A | 10/2007 |
| JP | 2008-523370 A | 7/2008 |
| JP | 04184427 B1 | 11/2008 |
| JP | 2009-000412 A | 1/2009 |
| JP | 2009-018173 A | 1/2009 |
| JP | 2011-087733 A | 5/2011 |
| JP | 2012512678 A | 6/2012 |
| JP | 2012-526977 A | 11/2012 |
| JP | 2013-007645 A | 1/2013 |
| KR | 10-1266966 B1 | 5/2013 |
| KR | 10-2016-041632 A | 4/2016 |
| KR | 10-2016-0071127 A | 6/2016 |
| WO | 9008512 A1 | 8/1990 |
| WO | 91-004713 A1 | 4/1991 |
| WO | 94-010935 A1 | 5/1994 |
| WO | 98-032394 A1 | 7/1998 |
| WO | 98-044865 A1 | 10/1998 |
| WO | 9858596 A1 | 12/1998 |
| WO | 9924786 A1 | 5/1999 |
| WO | 20008415 A1 | 2/2000 |
| WO | 2002-017776 A2 | 3/2002 |
| WO | 2002-062252 A1 | 8/2002 |
| WO | 2002-095475 A1 | 11/2002 |
| WO | 2003-003932 A2 | 1/2003 |
| WO | 2006-096558 A2 | 9/2006 |
| WO | 2006-133548 A1 | 12/2006 |
| WO | 2007090865 A1 | 8/2007 |
| WO | 2008129073 A2 | 10/2008 |
| WO | 2009-085752 A2 | 7/2009 |
| WO | 2009-089129 A1 | 7/2009 |
| WO | 2009-146788 A1 | 12/2009 |
| WO | 2009-146789 A1 | 12/2009 |
| WO | 2012-007003 A1 | 1/2012 |
| WO | 2012-064684 A2 | 5/2012 |
| WO | 2012-074304 A2 | 6/2012 |
| WO | 2014-091865 A1 | 6/2014 |
| WO | 2015-015289 A2 | 2/2015 |
| WO | 2015015289 A2 | 2/2015 |
| WO | 2015-063032 A1 | 5/2015 |
| WO | 2015-176004 A1 | 11/2015 |
| WO | 2016-004415 A1 | 1/2016 |
| WO | 2016-042393 A1 | 3/2016 |
| WO | 2016-061279 A1 | 4/2016 |
| WO | 2016-084066 A1 | 6/2016 |
| WO | 2016-099471 A1 | 6/2016 |
| WO | 2016-113745 A1 | 7/2016 |
| WO | 2016-116874 A1 | 7/2016 |
| WO | 2018-085718 A2 | 5/2018 |

OTHER PUBLICATIONS

Third-Party Submission Under 37 CFR 1.290 for U.S. Appl. No. 15/859,010, filed Jan. 11, 2019.

U.S. Department of Commerce, National Technical Information Service, "Holodontography: An Introduction to Dental Laser Holography", School of Aerospace Medicine Brooks AFB Tex; Mar. 1973, 37 pages.

Schmidt, et al. "Automated Crown Replication Using Solid Photography SM", National Technical Information Service, Solid Photography Inc., Melville NY,; Oct. 1977; 19 pages.

Van Der Linden, "A New Method to Determine Tooth Positions and Dental Arch Dimensions", Journal fo Dental Research; 51(4); p. 1104; Jul.-Aug. 1972.

Van Der Linden et al., "Three-Dimensional Analysis of Dental Casts by Means of the Optocom", Journal of Dental Research; 51 (4 ); p. 11 00; Jul.-Aug. 1972.

Van Der Zel, "Ceramic-Fused-to-Metal Restorations with a New CAD/Cam System", Quintessence International; 24(A); pp. 769-778; (year of pub. Sufficiently earlier than effective US filing date and any foreign priority date); 1993.

Van Hilsen et al., "Comparing potential early caries assessment methods for teledentistry", BMC Oral Health; 13(16); doi: 10.1186/1472-6831-13-16; 9 pages; Mar. 2013.

Varady et al.; "Reverse Engineering Of Geometric Models—An Introduction", Computer-Aided Design; 29(4 ); pp. 255-268; 29 pages; (Author Manuscript); May 13, 1996.

Verstreken et al., "An Image-Guided Planning System for Endosseous Oral Implants", IEEE Transactions on Medical Imaging; 17(5); pp. 842-852; Oct. 1998.

Warunek et al., "Physical and Mechanical Properties of Elastomers in Orthodonic Positioners", American Journal of Orthodontics and Dentofacial Orthopedics; 95(5); pp. 388-400; 21 pages; (Author Manuscript); May 1989.

Warunek et.al., "Clinical Use of Silicone Elastomer Applicances", JCO; 23 (10); pp. 694-700; Oct. 1989.

Wells, "Application of the Positioner Appliance in Orthodontic Treatment", American Journal of Orthodontics; 58( 4 ); pp. 351-366; Oct. 1970.

Wishan, "New Advances in Personal Computer Applications for Cephalometric Analysis, Growth Prediction, Surgical Treatment Planning and Imaging Processing", Symposium: Computerized Facial Imaging in Oral and Maxilofacial Surgery; p. 5; Presented on Sep. 13, 1990.

Wikipedia; Palatal expansion; 3 pages; retrieved from the internet (https://en.wikipedia.org/wiki/Palatal_expansion) on Mar. 5, 2018.

Williams, "Dentistry and CAD/Cam: Another French Revolution", J. Dent. Practice Admin.; 4(1); pp. 2-5 Jan./Mar. 1987.

Williams, "The Switzerland and Minnesota Developments in CAD/CAM", Journal of Dental Practice Administration; 4(2); pp. 50-55; Apr./Jun. 1987.

Wireless Sensor Networks Magazine, "Embedded Teeth for Oral Activity Recognition", Jul. 29, 2013, 2 pages; retrieved on Sep. 19, 2016 from the internet (www.wsnmagazine.com/embedded-teeth/).

(56) References Cited

OTHER PUBLICATIONS

Witt et al., "The wear-timing measuring device in orthodontics—cui bono? Reflections on the state-of-the-art in wear-timing measurement and compliance research in orthodontics"; Fortschr Kieferothop; 52(3); pp. 117-125; (Translation Included) Jun. 1991.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al., "Three-Dimensional Virtual-Reality Surgical Planning and Soft-Tissue Prediction for Orthognathic Surgery", IEEE Transactions on Information Technology in Biomedicine; 5(2); pp. 97-107; Jun. 2001.
Yamada et al., "Simulation of fan-beam type optical computer-tomography imaging of strongly scattering and weakly absorbing media", Applied Optics; 32(25); pp. 4808-4814; Sep. 1, 1993.
Yamamoto et al., "Optical Measurement of Dental Cast Profile and Application to Analysis of Three-Dimensional Tooth Movement in Orthodontics", Front. Med. Biol. Eng., 1(2); pp. 119-130; (year of pub. sufficiently earlier than effective US filing date and any foreign priority date); 1988.
Yamamoto et al., "Three-Dimensional Measurement of Dental Cast Profiles and Its Applications to Orthodontics", Conf. Proc. IEEE Eng. Med. Bioi. Soc.; 12(5); pp. 2052-2053; Nov. 1990.
Yamany et al., "A System for Human Jaw Modeling Using Intra-Oral Images", Proc. Of the 20th Annual Conf. of the IEEE Engineering in Medicine and Biology Society; vol. 2; pp. 563-566; Oct. 1998.
Yoshii, "Research on a New Orthodontic Appliance: The Dynamic Positioner (D.P.); I. The D.P. Concept and Implementation of Transparent Silicone Resin (Orthocon)"; Nippon Dental Review; 452; pp. 61-74; 32 pages; (Author Manuscript); Jun. 1980.
Yoshii, "Research on a New Orthodontic Appliance: The Dynamic Positioner (D.P.); II. The D.P. Manufacturing Procedure and Clinical Applications", Nippon Dental Review; 454; pp. 107-130; 48 pages; (Author Manuscript); Aug. 1980.
Yoshii, "Research on a New Orthodontic Appliance: The Dynamic Positioner (D.P.)—III. The General Concept of the D.P. Method and Its Therapeutic Effect, Part 1, Dental and Functional Reversed Occlusion Case Reports", Nippon Dental Review; 457; pp. 146-164; 43 pages; (Author Manuscript); Nov. 1980.
Yoshii, "Research on a New Orthodontic Appliance: The Dynamic Positioner (D.P.); III—The General Concept of the D.P. Method and Its Therapeutic Effect, Part 2. Skeletal Reversed Occlusion Case Reports", Nippon Dental Review; 458; pp. 112-129; 40 pages; (Author Manuscript); Dec. 1980.
Park, H. et al. "Development of High Speed and High Accuracy 3D Dental Intra Oral Scanner," Procedia Eng. 100 (2015) 1174-1181.
Chishti et al.; U.S. Appl. No. 60/050,342 entitled "Procedure for Moving Teeth Using a Seires of Retainers," filed Jun. 20, 1997.
Cottingham, "Gnathologic Clear Plastic Positioner", American Journal of Orthodontics; 55(1 ); pp. 23-31; Jan. 1969.
Crawford; CAD/CAM in the Dental Office: Does It Work?; Canadian Dental Journal; 57(2); pp. 121-123 Feb. 1991.
Crawford, Computers in Dentistry: Part 1: CAD/CAM: The Computer Moves Chairside, Part 2: F. Duret—A Man With A Vision, Part 3: The Computer Gives New Vision—Literally, Part 4: Bytes 'N Bites The Computer Moves From The Front Desk To The Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton, "Correcting Malaligned Mandibular Incisors with Removable Retainers", Journal of Clinical Orthodontics; 30(7); pp. 390-395; Jul. 1996.
Curry et al., "Integrated Three-Dimensional Craniofacial Mapping at the Craniofacial Research Instrumentation Laboratory / University of the Pacific", Seminars in Orthodontics; 7(4 ); pp. 258-265; Dec. 2001.
Cutting et al., "Three-Dimensional Computer-Assisted Design of Craniofacial Surgical Procedures: Optimization and Interaction with Cephalometric and CT-Based Models", Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al., "Three-Dimensional Large Displacement Analysis of Orthodontic Appliances", Journal of Biomechanics; 9( 12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-x; "DentSim . . . Dent-x's virtual reality 3-D training simulator . . . A revolution in dental education", 6 pages; retrieved from the internet (http://www.dent-x.com/DentSim.htm); on Sep. 24, 1998.
Doruk et al., "The role of the headgear timer in extraoral cooperation", European Journal of Orthodontics; 26; pp. 289-291; Jun. 1, 2014.
Doyle; "Digital Dentistry, Doctors use CAD/CAM to take the pain out of extensive dental procedures", Computer Graphics World; pp. 50-52 and p. 54; Oct. 2000.
Dummer et al., "Computed Radiography Imaging Based on High-Density 670 nm VCSEL Arrays", International Society for Optics and Photonics; vol. 7557, p. 75570H, 7 pages; (Author Manuscript); Feb. 24, 2010.
Duret et al., "CAD/CAM Imaging in Dentistry", Current Opinion in Dentistry; 1 (2); pp. 150-154; Apr. 1991.
Duret et al.; CAD-CAM in Dentistry; Journal of the American Dental Association; 117(6); pp. 715-720; Nov. 1988.
Duret, "The Dental CAD/CAM, General Description of the Project", Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides, "The Microcomputer in the Orthodontic Office", Journal of Clinical Orthodontics; 13(11); pp. 767-772; Nov. 1979.
Elsasser, "Some Observations on the History and Uses of the Kesling Positioner", American Journal of Orthodontics; 36(5); pp. 368-374; May 1, 1950.
Faber et al., "Computerized Interactive Orthodontic Treatment Planning", American Journal of Orthodontics; 73(1 ); pp. 36-46; Jan. 1978.
Felton et al., "A Computerized Analysis of the Shape and Stability of Mandibular Arch Form", American Journal of Orthodontics and Detofacial Orthopedics, Dec. 1987, pp. 478-483, vol. 92 No. 6, The C. V. Mosby Company.
Friede et al., "Accuracy of Cephalometric Prediction in Orthognathic Surgery", Journal of Oral and Maxillofacial Surgery; 45(9); pp. 754-760; Sep. 1987.
Friedrich et al; "Measuring system for in vivo recording of force systems in orthodontic treatment—concept and analysis of accuracy", J. Biomech.; 32(1); pp. 81-85; (Abstract only) Jan. 1999.
Futterling et al, "Automated Finite Element Modeling of a Human Mandible with Dental Implants", JS WSCG '98—Conference Program; 8 pages; retrieved from the Internet (https://dspace5.zcu.ez/bitstream/11025/15851/1/Strasser_98.pdf); on Aug. 21, 2018.
Gao et al., "3-D Element Generation for Multi-Connected Complex Dental and Mandibular Structure", IEEE Proceedings International Workshop in Medical Imaging and Augmented Reality; pp. 267-271; Jun. 12, 2001.
GIM-ALLDENT Deutschland, "Das DUX System: Die Technik," 3 pages; (English Translation Included}; (year of pub. sufficiently earlier than effective US filing date and any foreign priority date); 2002.
Gottleib et al., JCO Interviews Dr. James A. McNamara, Jr., on the Frankel Appliance: Part 2: Clinical Management:, Journal of Clinical Orthodontics; 16(6), Jun. 1982, pp. 390-407; retrieved from the internet (http://www.jco-online.com/archive/print_article.asp?Year=1982&Month=06&ArticleNum+ ) on Mar. 9, 2005.
Grayson, "New Methods for Three Dimensional Analysis of Craniofacial Deformity", Symposium: Computerized Facial Imaging in Oral and

(56) References Cited

OTHER PUBLICATIONS

Maxillofacial Surgery; American Association of Oral and Maxillofacial Surgeons; 48(8) suppl 1; pp. 5-6; Sep. 13, 1990.
Grest, Daniel, Marker-Free Human Motion Capture in Dynamic Cluttered Environments from a Single View-Point:, PhD Thesis; 167 pages; Dec. 2007, Kiel, Germany.
Guess et al. "Computer Treatment Estimates In Orthodontics and Orthognathic Surgery" Journal of Clinical Orthodontics; 23(4); pp. 262-268; 11 pages; (Author Manuscript); Apr. 1989.
Heaven et al.; Computer-Based Image Analysis of Artificial Root Surface Caries; Abstracts of Papers #2094; Journal of Dental Research; vol. 70, Special Issue; p. 528; (Abstract Only); Apr. 17-21, 1991.
Highbeam Research, "Simulating stress put on jaw. (ANSYS Inc.'s finite element analysis software)" Nov. 1, 1996, 2 pages; retrieved from the Internet (http://static.highbeam.eom/titoolingampproduction/november011996/simulatingstressputonfa..); on Nov. 5, 2004.
Hikage, "Integrated Orthodontic Management System for Virtual Three-Dimensional Computer Graphic Simulation and Optical Video Image Database for Diagnosis and Treatment Planning" Journal of Japan KA Orthodontic Society 46(2); pp. 248-269; 56 pages; (English Translation Included); Feb. 26, 1987.
Hoffmann et al., "Role of Cephalometry for Planning of Jaw Orthopedics and Jaw Surgery Procedures", Informatbnen, pp. 375-396; (English Abstract Included); Mar. 1991.
Hojjatie et al., Three-Dimensional Finite Element Analysis of Glass-Ceramic Dental Crowns; Journal of Biomechanics; 23(11); pp. 1157-1166; Jan. 1990.
Huckins, "CAD-CAM Generated Mandibular Model Prototype from MRI Data", AAOMS, p. 96; (Abstract Only); (year of pub. sufficiently earlier than effective US filing date and any foreign priority date) 1999.
Invisalign; "You were made to move. There's never been a better time to straighten your teeth with the most advanced clear aligner in the world"; Product webpage; 2 pages; retrieved from the internet (www.invisalign.com/) on Dec. 28, 2017.
JCO Interviews, "Craig Andreiko , DDS, MS on the Elan and Orthos Systems; Interview by Dr. Larry W. White", Journal of Clinical Orthodontics; 28(8); pp. 459-468; 14 pages; (Author Manuscript); Aug. 1994.
JCO Interviews; "Dr. Horner W. Phillips on Computers in Orthodontic Practice, Part 2", Journal of Clinical Orthodontics; 17(12); pp. 819-831; 19 pages; Dec. 1983.
Jerrold, "The Problem, Electronic Data Transmission and the Law", American Journal of Orthodontics and Dentofacial Orthopedics; 113(4 ); 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kamada et al., "Case reports on Tooth Positioners Using LTV Vinyl Silicone Rubber", J. Nihon University School of Dentistry; 26(1); pp. 11-29; (year of pub. Sufficiently earlier than effective US filing date and any foreign priority date) 1984.
Kamada et al. "Construction of Tooth Positioners with OTV Vinyl Silicone Rubber and Some Case Reports", J. Nihon University School of Dentistry; 24(1); pp. 1-27; (year of pub. Sufficiently earlier than effective US filing date anda ny foreign priority date) 1982.
Kanazawa et al., "Three-Dimensional Measurements of the Occlusal Surfaces of Upper Molars in a Dutch Population", Journal of Dental Research; 63(11); pp. 1298-1301; Nov. 1984.
Kesling et al., "The Philosophy of the Tooth Positioning Appliance", American Journal of Orthodontics and Oral Surgery; 31 (6); pp. 297-304; Jun. 1945.
Kesling, "Coordinating the Predetermined Pattern and Tooth Positioner with Conventional Treatment", American Journal of Orthodontics and Oral Surgery; 32(5); pp. 285-293; May 1946.

Tiziani H. J. et al., "Confocal principle for macro- and microscopic surface and defect analysis," Optical Engineering, Jan. 1, 2000, pp. 32-39, vol. 39(1), Society of Photo-Optical Instrumentation Engineers.
Siemens; Cerec—"Computer-Reconstruction,"High Tech in der Zahnmedizin, 15 pages; (Includes Machine Translation); (year of pub. sufficiently earlier than effective US filing date and any foreign priority date); 2004.
Sinclair, "The Readers' Corner", Journal of Clinical Orthodontics; 26(6); pp. 369-372; 5 pages; retrived from the internet (http://www.jco-online.comlarchive/print_article .asp?Year= 1992&Month=06 &ArticleNum=); Jun. 1992.
Stoll et al.; "Computer-aided Technologies in Dentistry", Dtsch Zahna'rztl Z 45, pp. 314-322; (English Abstract Included); (year of pub. sufficiently earlier than effective US filing date and any foreign priority date) 1990.
Sturman, "Interactive Keyframe Animation of 3-D Articulated Models", Proceedings Graphics Interface '84; vol. 86; pp. 35-40; May-Jun. 1984.
The American Heritage, Stedman's Medical Dictionary; "Gingiva"; 3 pages; retrieved from the interent (http://reference.com/search/search?q=gingiva) on Nov. 5, 2004.
The Dental Company Sirona, "Cerec Omnicam and Cerec Bluecam. The first choice in every case", product brochure, 8 pages; (year of pub. sufficiently earlier than effective US filing date and any foreign priority date) 2014.
Thera Mon; "Microsensor"; "2 pages"; retrieved from the internet (www.english.thera-mon.com/the-product/transponder/index.html); on Sep. 19, 2016.
AADR, American Association for Dental Research; Summary of Activities; Los Angeles, CA; p. 195; Mar. 20-23, 1980.
Alcaniz et al., "An Advanced System for the Simulation and Planning of Orthodontic Treatments" Visualization in Biomedical Computing, 4th Intl. Conf, VBC '96, Sep. 22-25, 1996, pp. 511-520, Springer-Verlag, Hamburg, Germany.
Alexander et al.,"The DigiGraph Work Station Part 2 Clinical Management", J. Clin. Orthod., Jul. 1990, 12 pages.
Allesee Orthodontic Appliances: "Important Tip About Wearing the Red White & Blue Active Clear Retainer System", Allesee Orthodontic Appliances—Pro Lab; 1 page; (year of pub. Sufficiently earlier than effecitve US filing date and any foreign priroirty date); 1998.
Allesee Orthodontic Appliances; The Choice is Clear: Red, White & Blue . . . the Simple, Affordable, No-Braces Treatment; (Patient Information); retrieved from the internet (http://ormco.com/aoa/appliancesservices/RWB/patients.html); 2 pages on May 19, 2003.
Allesee Orthodontic Appliances; The Choice is Clear: Red, White & Blue . . . the Simple, Affordable, No-Braces Treatment; (product information for doctors); retrieved from the internet (http://ormco.com/aoa/appliancesservices/RWB/doctrohtml); 5 pages on May 19, 2003.
Allesee Orthodontic Appliances; The Choice is Clear: Red, White & Blue . . . the Simple, Affordable, No-Braces Treatment; (product information), 6 pages; (year of pub. Sufficiently earlier than effective US filing date and any foreign priority date) 2003.
Allesee Orthodontic Appliances; The Red, White & Blue Way to Improve Your Smile; (information for patients), 2 pages; (year of pub. Sufficiently earlier than effective US filing date and any foreign priority date) 1992.
Allesee Orthodontic Appliances; You may be a candidate for this invisible no-braces treatment; product information for patients; 2 pages; (year of pub. Sufficiently earlier than effective US filing date and any foreign priority date) 2002.
Allesee Orthodontic Applicances: Dura ClearTM; Product information; 1 page; (year of pub. Sufficiently earlier than effective US filing date and any foreign priority date) 1997.
Altschuler et al., Analysis of 3-D Data for Comparative 3-D Serial Growth Pattern Studies of Oral-Facial Structures; IADR Abstracts, Program and Abstracts of Papers, 57th General Session, AIDR Annual Session, Mar. 29, 1979-Apr. 1, 1979, New Orleans Marriot; Journal of Dental Research; vol. 58, Special Issue A, p. 221; Jan. 1979.

(56) References Cited

OTHER PUBLICATIONS

Altschuler et al., Laser Electro-Optic System for Rapid Three-Dimensional (3D) Topographic Mapping of Surfaces; Optical Engineering; Dec. 1981, pp. 953-961, vol. 20(6).
Altschuler et al., "Measuring Surfaces Space-Coded by a Laser-Projected Dot Matrix" SPIE Imaging Applications for Automated Industrial Inspection and Assembly; Oct. 10, 1979, pp. 187-191, vol. 182.
Altschuler; 3D Mapping of Maxillo-Facial Prosthesis; AADR Abstract #607; 1 page, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, "The Six Keys to Optimal Occlusion" Straight Wire, Chapter 3, L.A. Wells; pp. 13-24; year of pub. sufficiently earlier than effective US filing date and any foreign priority date) 1989.
Barone et al., "Creation of 30 Multi-Body Orthodontic Models by Using Independent Imaging Sensors"; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al., "Mapping the Skull in 3-D," reprinted from J. Calif. Dent. Assoc, 48(2), 11 pages; (year of pub. sufficiently earlier than effective US filing date and any foreign priority date) Fall Issue 1972, vol. 48, No. 2.
Baumrind et al., "A Stereophotogrammetric System for the Detection of Prosthesis Loosening in Total Hip Arthroplasty", NATO Symposium on Applications of Human Biostereometrics; SPIE; vol. 166; pp. 112-123; Jul. 9-13, 1978.
Baumrind, "A System for Crania facial Mapping Through the Integration of Data from Stereo X-Ray Films and Stereo Photographs", an invited paper submitted to the 1975 American Society of Photogram Symposium on Close-Range Photogram Systems; University of Illinois; pp. 142-166; Aug. 26-30, 1975.
Baumrind, "Integrated Three-Dimensional Craniofacial Mapping: Background, Principles, and Perspectives", Seminars in Orthodontics; 7(4 ); pp. 223-232; Dec. 2001.
Begole et al.; A Computer System for the Analysis of Dental Casts; The Angle Orthodontist; 51(3); pp. 252-258, Jul. 1981.
Bernard et al., "Computerized Diagnosis in Orthodontics for Epidemiological Studies: A ProgressReport" (Abstract Only), J. Dental Res. Special Issue, vol. 67, p. 169, paper presented at International Association for Dental Research 66th General Session, Montreal Canada; Mar. 9-13, 1988.
Bhatia et al., "A Computer-Aided Design for Orthognathic Surgery", British Journal of Oral and Maxillofacial Surgery 22(4 ); pp. 237-253; Aug. 1, 1984.
Biggerstaff et al., "Computerized Analysis of Occlusion in the Postcanine Dentition", American Journal of Orthodontics; 61 (3); pp. 245-254; Mar. 1972.
Biggerstaff, "Computerized Diagnostic Setups and Simulations", Angle Orthodontist; 40(I); pp. 28-36; Jan. 1970.
Biostar Operation & Training Manual. Great Lakes Orthodontics, Ltd. 199 Fire Tower Drive, Tonawanda, New York. 14150-5890, 20 pages; (year of pub. sufficiently earlier than effective US filing date and any foreign priority date) 1990.
Blu et al.; "Linear Interpolation Revitalized", IEEE Transactions on Image Processing; 13(5); pp. 710-719; May 2004.
Bourke, "Coordinate System Transformation", 2 pages, Jun. 1996, retrieved from the internet (http://local.wasp.uwa.edu.au/~pbourke/protection/coords/) on Sep. 19, 2006.
Boyd et al., "Three Dimensional Diagnosis and Orthodontic Treatment of Complex Malocclusions With the Invisalipn Appliance", Seminars in Orthodontics; 7(4); pp. 274-293; Dec. 2001.
Brandestini et al. "Computer Machined Ceramic Inlays: In Vitro Marginal Adaptation", J. Dent. Res. Special Issue (Abstract 305); vol. 64; p. 208; (year of pub. sufficiently earlier than effective US filing date and any foreign priority date) 1985.

Brook et al., "An Image Analysis System for the Determination of Tooth Dimensions from Study Casts: Comparison with Manual Measurements of Mesio-distal Diameter", Journal of Dental Research; 65(3); pp. 428-431: Mar. 1986.
Burstone et al., "Precision Adjustment of the Transpalatal Lingual Arch: Computer Arch Form Predetermination", American Journal of Orthodontics; 79(2);pp. 115-133; Feb. 1981.
Burstone; "Dr. Charles J. Burstone on The Uses of the Computer in Orthodontic Practice (Part 1 )"; Journal of Clinical Orthodontics; 13(7); pp. 442-453; (interview); Jul. 1979.
Burstone; "Dr. Charles J. Burstone on The Uses of the Computer in Orthodontic Practice (Part 2)"; Journal of Clinical Orthodontics; 13(8); pp. 539-551 (interview); Aug. 1979.
"Cardinal Industrial Finishes for Liquid and Powder Coatings", The Powder Coating Isntitute; 6 pages; retrieved from the internet (http://www.cardinalpaint.com/powder%20coatings.htm) on Aug. 25, 2000.
Carnaghan et al., "An Alternative to Holograms for the Portrayal of Human Teeth", 4th Int'l. Conf. on Holographic Systems, Components and Applications; pp. 228-231; Sep. 15, 1993.
Thorlabs; Pellin broca prisms; 1 page; retrieved from the internet (www.thorlabs.com); Nov. 30, 2012.
Chaconas et al, "The DigiGraph Work Station, Part 1, Basic Concepts"; Journal of Clinical Orthodontics; 24(6); pp. 360-367; (Author Manuscript); Jun. 1990.
Chafetz et al., "Subsidence of the Femoral Prosthesis, A Stereophotogrammetric Evaluation", Clinical Orthopaedics and Related Research; No. 201; pp. 60-67; Dec. 1985.
Chiappone, "Constructing the Gnathologic Setup and Positioner", Journal of Clinical Orthodontics; 14(2); pp. 121-133; Feb. 1980.
Kleeman et al., "The Speed Positioner", J. Clin. Orthod.; 30(12); pp. 673-680; Dec. 1996.
Kochanek et al., "Interpolating Splines with Local Tension, Continuity and Bias Control", Computer Graphics; 18(3); pp. 33-41; Jan. 1, 1984.
Kumar et al.; Rapid maxillary expansion: A unique treatment modality in dentistry; J. Clin. Diagn. Res.; 5(4); pp. 906-911; Aug. 2011.
Kunii et al., "Articulation Simulation for an Intelligent Dental Care System" Displays; 15(3); pp. 181-188; Jul. 1994.
Truax, "Truax Clasp-Less(TM) Appliance System", The Functional Orthodontist; 9(5); pp. 22-24, 26-28; Sep.-Oct. 1992.
Kuroda et al., "Three-Dimensional Dental Cast Analyzing System Using Laser Scanning", American Journal of Orthodontics and Dentofacial Orthopedics; 11 0(4 ); pp. 365-369; Oct. 1996.
Laurendeau et al., "A Computer-Vision Technique for the Acquisition and Processing of 3-D Profiles of Dental Imprints: An Application in Orthodontics", IEEE Transactions on Medical Imaging; 1 0(3); pp. 453-461; Sep. 1991.
Leinfelder et al., "A New Method for Generating Ceramic Restorations: a CAD-CAM System" Journal of the American Dental Association; 118(6); pp. 703-707; Jun. 1989.
Manetti et al., "Computer-Aided Cefalometry and New Mechanics in Orthodontics" Fortschr Kieferorthop; 44; pp. 370-376; 8 pages; (English Article Summary Included); (year of pub. sufficiently earlier than effective US filing date and any foreign priority date) 1983.
McCann; Inside the ADA; J. Amer. Dent. Assoc, 118:286-294; Mar. 1989.
McNamara et al., "Invisible Retainers", J. Clin Orthod.; pp. 570-578; 11 pages; (Author Manuscript); Aug. 1985.
McNamara et al.; "Orthodontic and Orthopedic Treatment in the Mixed Dentition", Needham Press; pp. 347-353; Jan. 1993.
Moermann et al, "Computer Machined Adhesive Porcelain Inlays: Margin Adaptation after Fatigue Stress", IADR Abstract 339; J. Dent. Res.; 66(a):763; (Abstract Only); (year of pub. sufficiently earlier than effective US filing date and any foreign priority date) 1987.
Moles, "Correcting Mild Malalignments—As Easy As One, Two, Three", AOA/Pro Corner; 11 (2); 2 pages; (year of pub. sufficiently earlier than effective US filing date and any foreign priority date) 2002.

(56) References Cited

OTHER PUBLICATIONS

Mormann et al.; "Marginale Adaptation von adhasuven Porzellaninlays in vitro", Separatdruck aus:Schweiz. Mschr. Zahnmed.; 95; pp. 1118-1129: 8 pages; (Machine Translated English Abstract); (year of pub. sufficiently earlier than effective US filing date and any foreign priority date); 1985.
Nahoum, "The Vacuum Formed Dental Contour Appliance", N.Y. State Dent. J.; 30(9); pp. 385-390; Nov. 1964.
Nash, "CEREC CAD/CAM Inlays: Aesthetics and Durability in a Single Appointment", Dentistry Today; 9(8); pp. 20, 22-23 and 54; Oct. 1990.
Nedelcu et al.; "Scanning Accuracy and Precision in 4 Intraoral Scanners: An In Vitro Comparison Based On 3-Dimensional Analysis"; J. Prosthet. Dent.; 112(6); pp. 1461-1471; Dec. 2014.
Nishiyama et al., "A New Construction of Tooth Repositioner by LTV Vinyl Silicone Rubber", Journal of Nihon University School of Dentistry; 19(2); pp. 93-102 (year of pub. Sufficiently earlier than effective US filing date and any foreign priority date) 1977.
Ogawa et al., "Mapping, profiling and clustering of pressure pain threshold (PPT) in edentulous oral muscosa", Journal of Dentistry; 32(3); pp. 219-228; Mar. 2004.
Ogimoto et al., "Pressure-pain threshold determination in the oral mucosa: validity and reliability", Journal of Oral Rehabilitation; 29(7); pp. 620-626; Jul. 2002.
Paul et al.; "Digital Documentation of Individual Human Jaw and Tooth Forms for Applications in Orthodontics; Oral Surgery and Forensic Medicine" Proc. of the 24th Annual Conf. of the IEEE Industrial Electronics Society (IECON '98) vol. 4; pp. 2415-2418; Sep. 4, 1998.
Pinkham, "'Foolish' Concept Propels Technology", Dentist, 3 pages, Jan./Feb. 1989.
Pinkham, "Inventor's CAD/CAM May Transform Dentistry", Dentist; pp. 1 and 35, Sep. 1990.
Ponitz, "Invisible Retainers", American Journal of Orthodics, 59(3); pp. 266-272; Mar. 1971.
Procera Research Projects; Procera Research Projects 1993. Abstract Collection; 23 pages; (year of pub. sufficiently earlier than effective US filing date and any foreign priority date) 1993.
Proffit et al., "The First Stage of Comprehensive Treatment: Alignment and Leveling", Contemporary Orthodontics, 3rd Ed.; Chapter 16; Mosby Inc.; pp. 534-537; (year of pub. sufficiently earlier than effective US filing date and any foreign priority date) 2000.
Proffit et al.; "The First Stage of Comprehensive Treatment: Alignment and Leveling", Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http:llwww.essix.comlmagazineldefaulthtml) on Aug. 13, 1997.
Redmond et al.; "Clinical Implications of Digital Orthodontics", American Journal of Orthodontics and Dentofacial Orthopedics; 117(2); pp. 240-242; Feb. 2000.
Rekow et al., "CAD/CAM for Dental Restorations—Some of the Curious Challenges", IEEE Transactions on Biomedical Engineering; 38(4); pp. 314-318; Apr. 1991.
Rekow et al., "Comparison of Three Data Acquisition Techniques for 3-D Tooth Surface Mapping", Annual International Conference of the IEEE Engineering in Medicine and Biology Society; 13(1); pp. 344-345 (year of pub. sufficiently earlier than effective US filing date and any foreign priority date) 1991.
Rekow, "A Review of the Developments in Dental CAD/CAM Systems", Current Opinion in Dentistry; pp. 25-33; Jun. 1992.
Rekow, "CAD/CAM in Dentistry: A Historical Perspective and View of the Future", Journal Canadian Dental Association; 58(4); pp. 283, 287-288; Apr. 1992.
Rekow, "Computer-Aided Design and Manufacturing in Dentistry: A Review of the State of the Art", Journal of Prosthetic Dentistry; 58(4 ); pp. 512-516; Dec. 1987.
Rekow, "Dental CAD-CAM Systems: What is the State of the Art?", The Journal of the American Dental Association; 122(12); pp. 43-48; Dec. 1991.
Rekow, "Feasibility of an Automated System for Production of Dental Restorations", Ph.D. Thesis; Univ. of Minnesota, 250 pages, Nov. 1988.
Richmond et al., "The Development of a 3D Cast Analysis System", British Journal of Orthodontics; 13(1 ); pp. 53-54; Jan. 1986.
Richmond et al., "The Development of the PAR Index (Peer Assessment Rating): Reliability and Validity", The European Journal of Orthodontics; 41(2); pp. 125-139; Apr. 1992.
Richmond, "Recording The Dental Cast In Three Dimensions", American Journal of Orthodontics and Dentofacial Orthopedics; 92(3); pp. 199-206; Sep. 1987.
Rudge, "Dental Arch Analysis: Arch Form, A Review of the Literature" European Journal of Orthodontics; 3(4 ); pp. 279-284; Jan. 1981.
Sahm et al, "Micro-Electronic Monitoring Of Functional Appliance Wear"; Eur J Orthod.; 12(3); pp. 297-301; Aug. 1990.
Sahm, "Presentation of a wear timer for the clarification of scientific questions in orthodontic orthopedics", Fortschritte der Kieferorthopadie; 51 (4); pp. 243-247; (Translation Included) Jul. 1990.
Sakuda et al. "Integrated Information-Processing System In Clinical Orthodontics: An Approach with Use of a Computer Network System", American Journal of Orthodontics and Dentofacial Orthopedics; 101 (3); pp. 210-220; 20 pages; (Author Manuscript) Mar. 1992.
Schafer et al.; "Quantifying patient adherence during active orthodontic treatment with removable appliances using microelectronic wear-time documentation"; Eur J Orthod.; 37(1) pp. 1-8; doi:10.1093/ejo/cju012; Jul. 3, 2014.
Schellhas et al., "Three-Dimensional Computed Tomography in Maxillofacial Surgical Planning", Archives of Otolaryngology—Head and Neck Surgery; 114(4); pp. 438-442; Apr. 1988.
Schroeder et al; Eds. "The Visual Toolkit", Prentice Hall PTR, New Jersey; Chapters 6, 8 & 9, (pp. 153-210,309-354, and 355-428; (year of pub. sufficiently earlier than effective US filing date and any foreign priority date) 1998.
Tru-Tain Orthodontic & Dental Supplies, Product Brochure, Rochester, Minnesota 55902, 16 pages; (year of pub. sufficiently earlier than effective US filing date and any foreign priority date) 1996.
Shilliday, "Minimizing finishing problems with the mini-positioner", American Journal of Orthodontics; 59(6); pp. 596-599; Jun. 1971.
Shimada et al.; Application of Optical Coherence Tomography (OCT) for Diagnosis of Caries, Cracks, and Defects of Restorations, Current Oral Health Reports; 2(2); pp. 73-80; Jun. 2015.

\* cited by examiner

APPARATUS FOR DENTAL IMAGING

CROSS REFERENCE

This application is a continuation of U.S. patent application Ser. No. 16/820,505 filed Mar. 16, 2020, which is a continuation of U.S. patent application Ser. No. 14/741,172, filed Jun. 16, 2015, which claims the benefit of U.S. Provisional Application No. 62/021,608, filed Jul. 7, 2014, the contents of each of which are hereby incorporated by reference in their entirety.

FIELD OF THE INVENTION

Embodiments of the present invention are directed to methods and apparatus for dental imaging, such as for measuring surface topology of teeth.

BACKGROUND

In the fields of orthodontics and prosthodontics, different methods are known to determine a current teeth topology in a patient's mouth. One of the methods involves taking an impression of a patient's dentition. Using this impression, a plaster cast is made, representing a (positive) physical teeth model. This physical teeth model may then be used for a subsequent treatment plan.

If CAD (computer-aided design) and/or CAM (computer-aided manufacturing) techniques are to be employed, a digital dataset corresponding to the teeth may be obtained by scanning. For example, the (positive) physical teeth model in form of the plaster cast or a (negative) physical teeth model in form of the impression may be scanned or imaged using x-rays, computed tomography, magnetic resonance imaging, or laser scanning apparatuses. With the thus obtained image data, a computer model of the teeth or a part thereof may be established. However, such methods and apparatus can be somewhat time consuming and more expensive than would be ideal.

As an alternative, teeth in a patient's mouth may be imaged directly. For this purpose, different imaging apparatuses are known.

The prior apparatus for non-contact imaging with a probe having a sensing face have been less than ideal in at least some respects. The prior probe devices can be somewhat larger than would be ideal, and may have a large intraoral front tip which can make the prior devices somewhat cumbersome to use in at least some instances. Although an array of incident light beams passing through focusing optics can be used, the larger than ideal probe heads of such devices can provide less than ideal measurements of the oral cavity of a patient. Also, the prior devices that rely on beams to generate illuminated spots on the structure and the intensity of returning light rays propagating along an optical path can be somewhat cumbersome to use and maintain and can be somewhat more costly to manufacture than would be ideal.

Although three-dimensional (3D) data acquisition using triangulation has been proposed, such devices can be less compact than would be ideal and can be somewhat difficult to place in the mouth of the patient. Also, such devices can require alignment and can be less accurate and reliable than would be ideal in at least some instances.

In light of the above, improved methods and apparatus for measuring surfaces such as the intraoral cavity are needed. Ideally such methods and apparatus will overcome at least some of the deficiencies of the prior methods and apparatus and be more accurate, reliable, compact, easier to use with the patient's mouth and less costly than the prior devices.

SUMMARY

In accordance with embodiments, an apparatus for confocal imaging is provided, which may comprise an illumination module for generating an array of light beams, an optics system for confocal focusing of the array of light beams, and a probe head with a light-guiding part having an entrance face and an exit face. The illumination module, the optics system, and the probe head can be arranged such that the array of light beams from the illumination module passes through the optics system, enters the light-guiding part via the entrance face, and exits the light-guiding part via the exit face. Embodiments disclosed herein provide probes having decreased size which can facilitate measurement of surfaces which can be difficult to reach with prior devices such as an oral cavity of a patient. The embodiments disclosed herein also have the advantage of providing improved accuracy and reliability with decreased manufacturing costs. In many embodiments, a plurality of beams is directed toward a measurement surface in which each of the plurality of beams extends to a focal point and comprises a chief ray. The chief rays of the plurality of beams can diverge from each other between the probe and the focal points in order to decrease the size of the probe and inhibit spread of the outermost marginal rays. In many embodiments, the confocal imaging system comprises a non-telecentric configuration such that the off-axis chief ray angles of the light beams exiting the probe have an opposite orientation with respect to angles of the marginal rays entering the probe, such that a substantially decreased cross-sectional size of the probe can be provided. In many embodiments, laterally outermost marginal rays of each of the outer beams on either side of the optical axis extend along an optical path substantially parallel to the optical axis and substantially parallel to the optical axis, or divergent from the optical axis. In many embodiments, lateral spread of the array of beams is inhibited as each individual beam converges toward the focal point, and this spread can be inhibited when the focal point is shifted.

In a first aspect, embodiments provide an apparatus for confocal imaging, comprising an illumination module for generating an array of light beams, an optics system for confocal focusing of the array of light beams and a probe head with a light-guiding part having an entrance face and an exit face. The illumination module, the optics system and the probe head are arranged such that the array of light beams from the illumination module passes through the optics system, enters the light-guiding part via the entrance face and exits the light-guiding part via the exit face. The optics system is configured such that, after having passed through the optics system, the outermost marginal rays of the outermost light beams with respect to the optical axis of the optics system are parallel or divergent to the optical axis.

In another aspect, embodiments provide an apparatus for confocal imaging comprising an illumination module for generating an array of light beams, an optics system for confocal focusing of the array of light beams and a probe head with a light-guiding part having an entrance face and an exit face. The illumination module, the optics system and the probe head are arranged such that chief rays of the array of light beams are divergent to each other.

In another aspect, embodiments provide a method for confocal imaging. An illumination module is provided for generating an array of light beams. An optics system is provided for confocal focusing of the array of light beams and a probe head with a light-guiding part having an optical axis and an entrance face and an exit face. The optics system is configured such that, after having passed through the optics system, outermost marginal rays of outermost light beams with respect to the optical axis are parallel or divergent with respect to the optical axis between the probe and focal points of the light beams.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
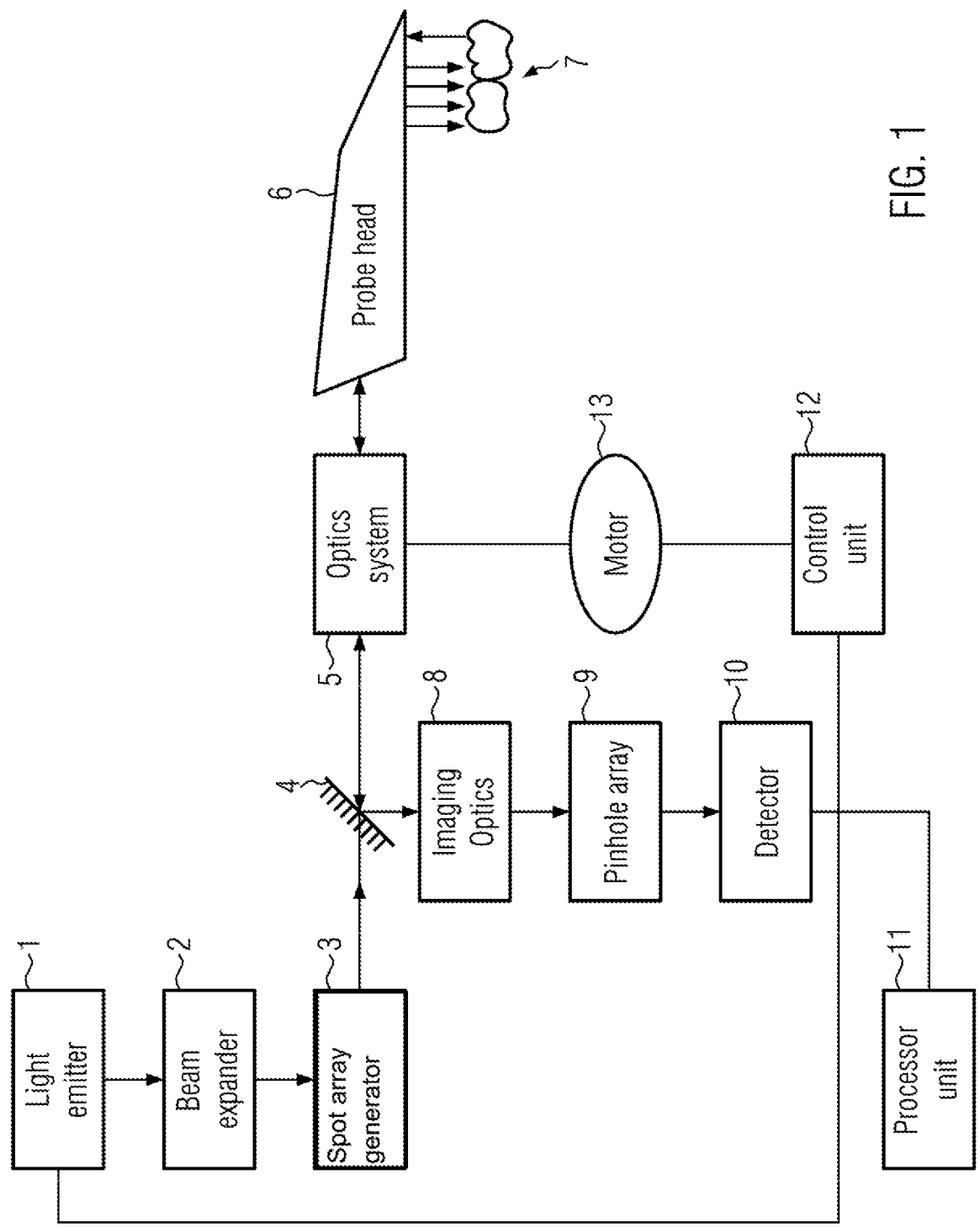
FIG. 1 is a schematic view of a confocal imaging apparatus, in accordance with embodiments.

The methods and apparatus disclosed herein can be combined in one or more of many ways and are well suited for combination with many devices related to surface topology such as the measurement of tissue surfaces such as surfaces of the oral cavity. The tissue surfaces may comprise one or more surfaces of teeth of the mouth, for example. The measured surfaces can be used by health care providers such as orthodontists and dentists.

In many embodiments, the optics system can be configured such that, after having passed through the optics system, the outermost marginal rays of the outermost light beams with respect to the optical axis of the optics system are parallel or divergent to the optical axis. In many embodiments, a plurality of light beams exits the probe head with divergent angles. Each of the plurality of light beams may comprise a chief ray divergent from an optical axis of the optics system.

In many embodiments, the outermost marginal rays of the outermost light beams, after exiting the optics system, do not converge towards the optical axis, in order to avoid a lateral spread of the array of beams even when shifting the focal plane of the focusing optics. In many embodiments, the term "outermost" refers to a distance transverse to the optical axis, such as a distance perpendicular to the optical axis. In many embodiments, an outermost light beam or most off-axis light beam comprises a beam having a largest distance to the optical axis in a direction perpendicular thereto.

The apparatus may be configured for intraoral confocal imaging, such as an apparatus for intraoral confocal imaging, which can be used for confocal imaging of positive and/or negative physical teeth models. The apparatus may comprise a scanning apparatus. The focusing optics of the apparatus may comprise non-telecentric optics, such that a reduced ray footprint at the probe head entrance face can be provided.

In many embodiments, the outermost marginal rays of the outermost light beams, after having passed through the optics system, are divergent with respect to the optical axis, and the divergence angle between the outermost marginal rays and the optical axis may be at most 10°, in some embodiments at most 8°, and in specific embodiments at most 5°.

In many embodiments, the light-guiding part comprises a transparent body. The transparent body may comprise one or more of glass or plastics, and may comprise a stiff, solid body, such as a rigid body.

The light-guiding part may be arranged such that the array of light beams enters the light-guiding part at an angle of approximately 90° with respect to the entrance face. In some embodiments, the light guiding part may be arranged such that the array of light beams enters via the entrance face at an angle of 90°±10°, such as 90°±8°, and more particularly of 90°±5°.

The light-guiding part may be bounded by sidewalls, and the sidewalls of the light-guiding part and entrance face may be arranged such that each light beam entering the light-guiding part via the entrance face is reflected at the sidewalls an odd number of times before exiting via the exit face. In many embodiments, each light beam may be reflected at the sidewalls three or five times before exiting via the exit face. Each of the sidewalls and/or the exit face and/or the entrance face may be planar.

The light-guiding part may be configured with an index of refraction and arrangement of the entrance face and sidewalls such that each light beam entering via the entrance face is reflected from at least one of the sidewalls of the light-guiding part by way of internal reflection. In many embodiments, at least some of the reflections at the sidewalls result from internal reflection such as one or more of total internal reflection, attenuated total internal reflection, or frustrated total internal reflection. Alternatively or additionally, at least some reflections may be provided with a mirror coating on a sidewall or part of a sidewall.

In many embodiments, the light-guiding part comprises a one-piece body.

In many embodiments, the light-guiding part comprises an upper sidewall being arranged at an acute angle with respect to the entrance face, a lower sidewall being arranged at an obtuse angle with respect to the entrance face, and an end sidewall being arranged at an acute angle with respect to the entrance face and/or the exit face. The upper sidewall may adjoin the entrance face; the lower sidewall may adjoin the entrance face and/or the end sidewall may adjoin the upper sidewall and/or the lower sidewall. The angle between the end sidewall and the upper sidewall may be an obtuse angle. The lower sidewall may comprise the exit face.

In many embodiments, the end sidewall may comprise a mirror. For example, the end sidewall may comprise a mirror coating. In such embodiments, the light-guiding part may be arranged and/or configured such that each light beam entering via the entrance face is reflected at all (remaining) sidewalls except for the end sidewall by way of internal reflection.

The angle between the entrance face and the lower sidewall may lie between 90° and 125°, in particular, between 90° and 115°. The angle between the exit face or the lower sidewall and the end sidewall may lie between 20° and 45°, in particular, between 25° and 35°. The angle between the entrance face and the upper sidewall may lie between 90° and 65°, in particular, between 90° and 80°.

The exit face may be covered by a transparent cover plate. The transparent cover plate may be a glass or plastics plate. The cover plate may be arranged at a distance from the exit face.

In many embodiments, the illumination module comprises a single light emitter or a plurality of light emitters. The one or more light emitters may emit coherent light. The light emitter may comprise one or a plurality of laser emitters. In embodiments comprising a single light emitter, the illumination module may further comprise a beam-expander element and/or a beam-splitter element for splitting a light beam from the light emitter into a plurality of light beams and/or an array of light beams. The beam-splitter element may comprise diffractive optics or a refractive optics, such as a grating or a microlens array.

Any of the above-described apparatuses may comprise a polarizer for linearly polarizing a light beam, wherein the polarizer is arranged along the optical path between the illumination module and the probe head, in particular, between the illumination module and the optics system.

Any of the above-described apparatuses may comprise a beam splitter being arranged along the optical path between the illumination module and the optics system such that the array of light beams from the illumination module passes through the beam splitter and an array of returning light beams from the optics module is reflected, in particular, towards a detector. The beam splitter may comprise a semi-transparent mirror. The light beams from the illumination module passing through the optics system may comprise incident light beams, and light beams following the optical path in an opposite direction through the optics system may comprise returning light beams. The array of returning light beams may comprise an array of light beams having been reflected by an object to be imaged, such as teeth portions, for example.

The described apparatuses may further comprise a detector for detecting an array of returning light beams. The detector may comprise an array of detector elements. The detector elements may comprise a CCD camera or a photodiode array. The detector may comprise a spectrophotometer.

The above-described apparatuses may comprise a focus-shifting mechanism for shifting the focal plane of the optics system. For example, the focus-shifting mechanism may be configured to shift one or more lenses of the optics system along the optical axis. In many embodiments, the focus-shifting mechanism may comprise a translation mechanism for translating the one or more lenses of the optics system.

In many embodiments, the probe heads comprise a housing, wherein the light guiding part and/or the optics system are provided within the housing. In embodiments where a focus-shifting mechanism is provided, the focus shifting mechanism may also be provided within the housing.

In many embodiments, the probe head comprises a part of a handheld device. The optics system and/or a focus-shifting mechanism may comprise part of the handheld device, for example. In particular, the handheld device may be defined by the housing described above.

Further features will be described with reference to the accompanying drawings, in accordance with embodiments.

As used herein, a chief ray encompasses a central ray of a beam of light. In many embodiments, a plurality of beams is directed onto the surface to be measured, in which each of the plurality of beams comprises a chief ray.

FIG. 1 schematically illustrates an example of an apparatus for dental confocal imagining of a teeth segment or teeth portion, in accordance with many embodiments. The teeth segment may comprise one tooth, a plurality of teeth, a tooth stump and/or a portion where one or more teeth are missing. The apparatus may be used, for example, for intraoral imaging of teeth. Alternatively, imaging of a positive or negative teeth model may be performed as well.

The illustrated apparatus comprises a light emitter 1 as a source of coherent light. As an example, the light emitter may be a laser source such as a semiconductor laser.

As indicated by the arrow shown, emitted light passes through a beam expander 2, which may comprise a collimating lens so as to obtain a collimated light beam having a desired width or numerical aperture.

Along the optical path between the light emitter 1 and the beam expander 2, optionally, a polarizer such as a polarization filter may be provided.

The beam expander 2 is followed by a spot array generator element 3 for splitting the beam into an array of light beams. The spot array generator element 3 in the form of diffraction or refraction optics may comprise a grating or a microlens array, for example.

In the illustrated example, the light emitter comprises a single light source from which the array of light beams is generated via the beam expander and the beam splitter element. As an alternative, the light emitter 1 may already comprise a plurality of light sources being arranged in form of an array. In this case, the array of light beams is generated directly at the light emitter 1 so that a beam expander and/or beam splitter may be avoided. As an example, the array of light sources may be provided in the form of an array of laser sources such as semiconductor lasers.

In this example, the light emitter 1, the beam expander 2 and the spot array generator element 3 define an illumination module generating an array of light beams.

The array of light beams, represented here, for ease of illustration, by a single line, passes through a beam splitter 4 in form of a semi-transparent mirror and enters optics system 5. The optics system 5 comprises a non-telecentric, confocal lens arrangement which will be described in more detail below.

The light beams coming from the light emitter 1 and propagating towards the sample to be imaged (e.g. a teeth segment) are called incident light beams, whereas light beams being reflected at the sample and propagating along the optical path of the incident light beams but in opposite direction are called returning light beams.

After the optics system 5, the incident array of light beams enters a probe head 6. In particular, the array of light beams is coupled into a light guiding part of the probe head via the light guiding part's entrance face. Within the light guiding part, each beam is reflected several times before it is coupled out via an exit face onto an object to be imaged, such as a teeth segment 7. In this way, an incident array of light beams is emitted towards the teeth segment 7, thus, resulting in an array of light spots on the teeth surface.

As also illustrated by one of the arrows between a tooth and the probe head, reflected light re-enters the probe head 6, particularly its light guiding part via the exit face. In this way, each reflected or returning light beam travels along the optical path in opposite direction as travelled by the incident light beams. Therefore, the returning light beams are also reflected several times within the light guiding part of probe head 6 and pass through optics system 5 in an inverse direction. At the semi-transparent mirror 4, the returned light beams are reflected towards imaging optics 8 comprising one or more lenses, followed by a pinhole array 9.

Then, the array of returning light beams impinges onto a detector 10, comprising an array of detector elements. For example, the detector 10 may be a CCD camera or a photodiode array. Each detector element or sensing element corresponds to a pinhole in the array 9.

The detector 10 is connected to a processing unit 11 where each light intensity measured in each of the detector elements is grabbed and analyzed.

The apparatus further comprises a control unit 12 being connected to the light emitter 1 as well as to a motor 13. Motor 13 is an example of a focus-shifting mechanism for shifting the focal plane of the optics system 5. In particular, motor 13 is coupled to the optics system 5 so as to shift or translate one or more lenses of the optics system along the optical axis. In this way, the focal plane location may be changed or shifted.

After receipt of a feedback signal that the location of the focal plane has changed (or that the one or more lenses have been shifted), control unit 12 triggers light emitter 1 to generate a light pulse. Processing unit 11 will grab data representative of the light intensity as detected by detector 10 corresponding to the light pulse which was reflected at the teeth portion 7. This procedure will be repeated for a plurality of locations for the focal plane.

As outlined in detail in WO 00/08415, the entire disclosure of which is incorporated herein by reference, for example, the surface topology of the image object (e.g. a teeth segment) is determined by determining the focal plane location for which, for a particular pixel, the light intensity is maximal. In this way, a three-dimensional representation of the object, e.g., the teeth segment, may be obtained. It may be displayed and/or further processed.

The array of light beams may comprise light beams having different wavelengths. For this purpose, the light emitter 1 may comprise different light sources emitting light of different wavelengths. In case of an array with beams of different wavelengths, the detector may be a spectrophotometer with color resolution. Examples for spectrophotometers are a three-chip CCD camera or the use of a Bayer mask over a monochrome CCD or other light sensor.

By using light components or light beams with different wavelengths, each being focused simultaneously on a different focal plane, the time for imaging may be reduced as different focal plane ranges can be simultaneously measured.

The probe head 6 may comprise a housing. For example, both the optics system 5 and the light guiding part may be provided within such a housing. The housing may be configured as a handheld device so that the light guiding part and/or optics system 5 and/or motor 13 are included in the handheld device.

Figure 2A:
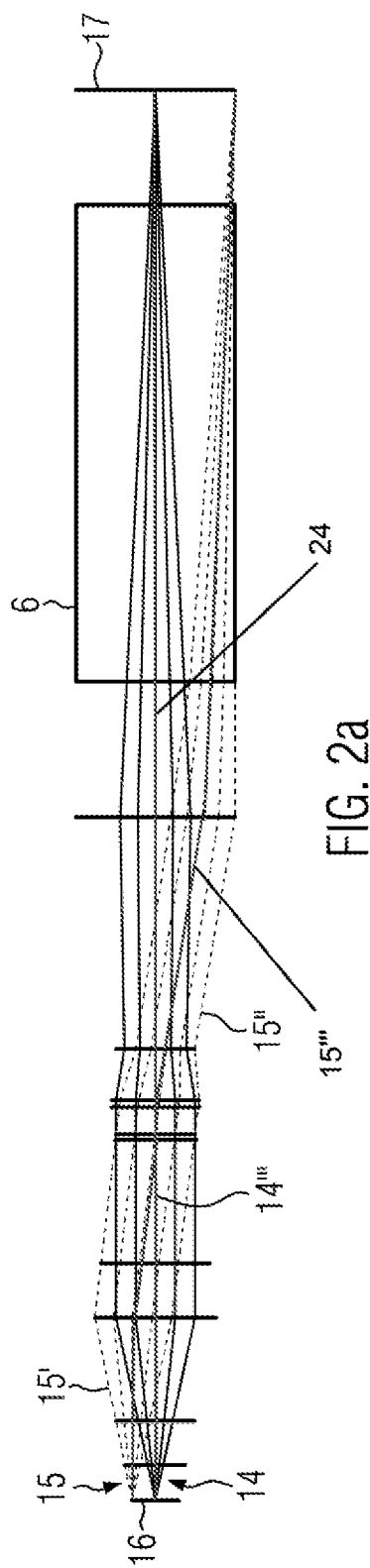
FIG. 2A is a schematic view of the optical path in an optics system of a confocal imaging apparatus in a paraxial design, in accordance with embodiments.

FIG. 2A schematically illustrates a paraxial design example of the optics system, showing the first order imaging configuration, in accordance with many embodiments. In this schematic view, probe 6 is illustrated as a single block. In this example, a central beam 14 and an outermost beam 15 (in a direction perpendicular to the optical axis) are emitted from a source plane 16. By way of example, reference numerals 15' and 15" denote marginal rays of the outermost beam 15, whereas reference numeral 14''' denotes the chief ray of central beam 14. Thus, the term "marginal rays" is used in the conventional sense denoting the rays (of a specific light beam) defining the beam's circumference or envelope; the "chief ray" corresponds to the central ray of a beam.

As can be seen in this example, the outermost marginal ray 15" of outermost light beam 15, after having passed through the optics system 5 and before entering the probe head 6, is parallel to the optical axis 24, and the marginal ray 15" is parallel to chief ray 14''' of the central beam that is on the optical axis 24.

In case of the complete array of light beams, the outermost marginal rays of the outer beams of the array (on either side of the optical axis) after having passed through the optics system and before entering probe head, are all parallel to the optical axis. As a consequence of this configuration, there is little or no lateral spread of the array of beams even when shifting the focal plane 17 of the array.

Each of the plurality of light beams may comprise a chief ray. For example, the outer beam 15 may comprise a chief ray 15' extending from an outer aperture at source plane 16 to the focus at focal plane 17.

As an alternative to or in combination with the above-described parallelism of the outermost marginal rays of the outermost beams and the chief ray of the central beam, the optics system may be configured such that the outermost marginal rays of the outermost light beams with respect to the optical axis of the optics system are divergent relative to the optical axis. In many embodiments, after having passed through the optics system, the outermost marginal ray of the outermost beams may show an opening angle with respect to the optical axis. This divergence angle or opening angle with respect to the optical axis may be at most 10°, preferably at most 8°.

In many embodiments, the confocal focusing system of the optics system comprises a non-telecentric optical system. The optics system can be configured such that the angle defined by the marginal rays of an outermost beam is complementary to the angle defined by the extreme off-axis chief rays with respect to the optical axis. In such embodiments, a decreased ray footprint at object to be imaged, e.g. the teeth segment, is provided.

Figure 2B:
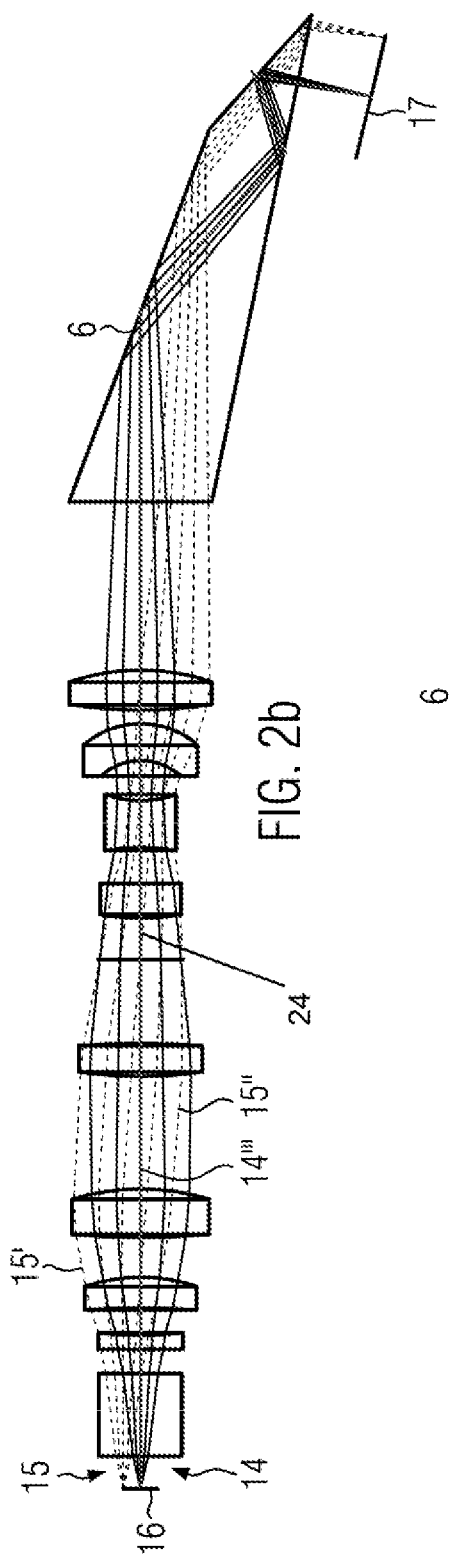
FIG. 2B is a schematic view of the optical path in an optics system of a confocal imaging apparatus in a thick lens design, in accordance with embodiments.

FIG. 2B schematically illustrates a thick lens design example corresponding to the embodiments of FIG. 2A. Also in FIG. 2B, from the array of beams generated by the illumination module, only one central beam 14 and one outermost beam 15 are shown with dashed lines for the sake of simplicity, in accordance with embodiments.

Figure 3:
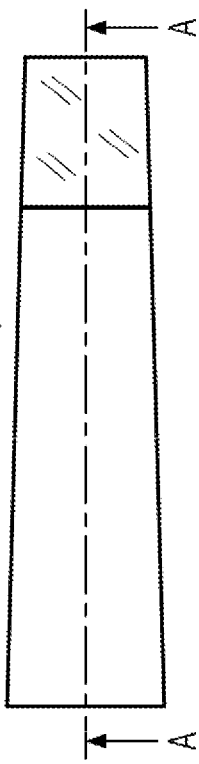
FIG. 3 is a top view of a schematically illustrated probe head, in accordance with embodiments.
Figure 4:
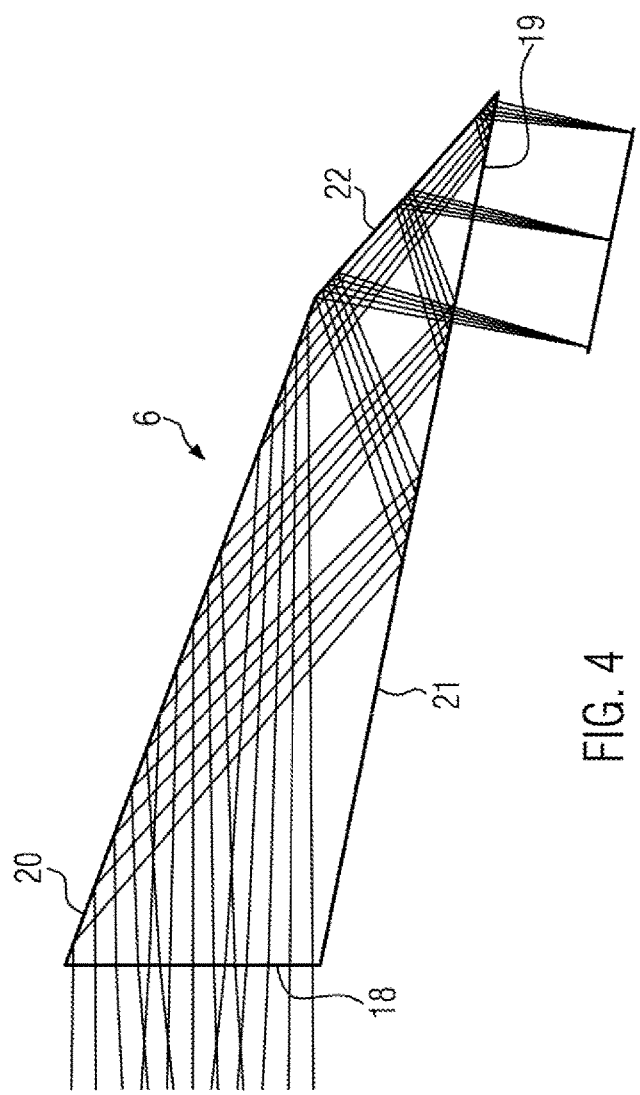
FIG. 4 is a longitudinal cross-section through line A-A in FIG. 3.

FIGS. 3 and 4 schematically illustrate a top view and a cross-sectional view (through line A-A) of a probe head, respectively, in accordance with many embodiments. The probe head 6 has a light-guiding part with an entrance face 18 and an exit face 19. Light coming from the light emitter and the optics system enters the light-guiding part via the entrance face 18 at an angle of about 90°, i.e., substantially normal to the entrance face. The entrance angle may be 90°±10°, preferably 90°±8°, for example. This particularly applies to the embodiments in which the outermost marginal rays of the outermost light beams are divergent with respect to the optical axis after having passed through the optics system.

As schematically illustrated in FIG. 4, the light-guiding part is arranged and light is coupled into the light guiding part in such a way that each light beam entering the light-guiding part via the entrance face 18 is reflected at the sidewalls. In embodiments according to FIG. 4, three reflections occur before a light beam exits the light-guiding part via the exit face 19. A first reflection takes place at an upper sidewall 20, adjoining the entrance face 18 and being arranged at an acute angle with respect to entrance face 18. The second reflection occurs at lower sidewall 21, also adjoining the entrance face 18 and being arranged at an obtuse angle with respect thereto. The last reflection occurs at end sidewall 22, adjoining both the upper and the lower sidewalls. The exit face 19 is part of the lower sidewall 21.

End sidewall 22 comprises a mirror, which may be obtained by a suitable coating of the corresponding surface of the light-guiding part. The light-guiding part as a whole, in these embodiments, may comprise a one-piece body, for example, comprising a glass body or a body composed of a transparent resin. The first and second reflections at upper sidewall 20 and lower sidewall 21 may result from internal reflection.

In view of these embodiments, the light-guiding part of the probe head, in accordance with its one-piece form, may be manufactured in a simple and economical way.

The specific configuration of the optics system as described above allows for a long light-guiding part and probe head while maintaining a small thickness resulting in an improved intraoral use.

Figure 5:
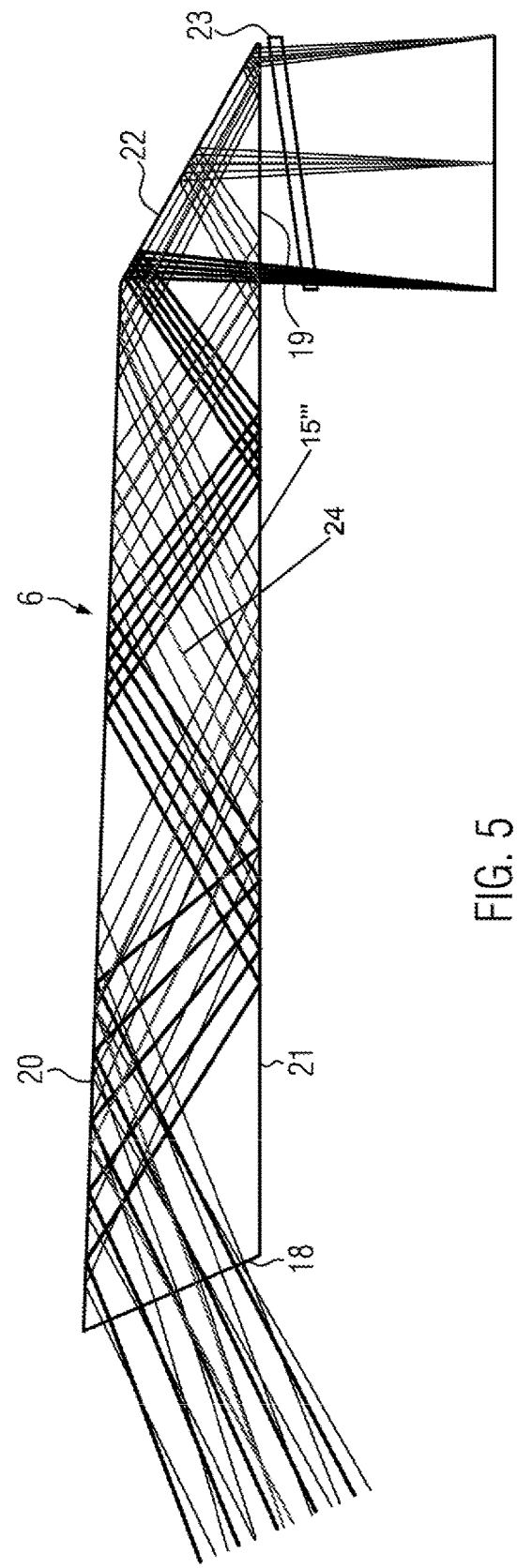
FIG. 5 is a longitudinal cross-section through a schematically illustrated probe head in accordance with embodiments.

In many embodiments, and as illustrated in FIG. 5, the exit face 19 may be covered by a transparent cover plate 23 which is arranged at some distance from the exit face 19. This cover plate 23 may be exchangeable for hygienic reasons, and may comprise a single use component.

The embodiments illustrated in FIG. 5 provides for an even longer light-guiding part along which the light beams are reflected five times before exiting via the exit face 19. In principle, any odd number of reflections is possible.

In many embodiments, the chief rays of each of a plurality of light beams exits the exit face 19 with a divergent angle with respect to the optical axis, for example. This divergence of each of the chief rays of the light beams provides improved measurements and can decrease the overlap of spots imaged onto the oral cavity, for example. The decrease of spread of the marginal rays the light beams as described herein can be combined with the divergence of the chief rays of each of the light beams in order to provide improved the accuracy of measurements as described herein, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for intraoral imaging, the apparatus comprising:
    a light source for generating light;
    an optics system for focusing the light; and
    a light-guiding part having an entrance face and an exit face,
    wherein the light source, the optics system and the light-guiding part are arranged such that the light passes through the optics system, enters the light-guiding part via the entrance face, and exits the light-guiding part via the exit face, and
    wherein the optics system is configured such that, upon entering the light-guiding part, an outermost chief ray of the light with respect to an optical axis of the optics system is divergent to the optical axis and an outermost marginal ray of the light with respect to the optical axis is parallel or divergent to the optical axis.

2. The apparatus according to claim 1, wherein the light-guiding part comprises a transparent body.

3. The apparatus according to claim 1, wherein the light-guiding part is arranged such that the light enters the light-guiding part at an angle of 90±10° with respect to the entrance face.

4. The apparatus according to claim 1, wherein the light-guiding part is bounded by sidewalls and the light-guiding part is arranged such that the light entering the light-guiding part via the entrance face is reflected at the sidewalls an odd number of times before exiting via the exit face.

5. The apparatus according to claim 4, wherein the light-guiding part is arranged such that the light entering via the entrance face is reflected with at least one of the sidewalls of the light-guiding part by way of internal reflection.

6. The apparatus according to claim 1, wherein the light-guiding part comprises a one-piece body.

7. The apparatus according to claim 1, wherein the light-guiding part comprises an upper sidewall arranged at an acute angle with respect to the entrance face, a lower sidewall arranged at an obtuse angle with respect to the entrance face, and an end sidewall arranged at an acute angle with respect to the entrance face or the exit face.

8. The apparatus according to claim 7, wherein the end sidewall comprises a mirror.

9. The apparatus according to claim 7, wherein the angle between the entrance face and the lower sidewall lies between 90° and 125°.

10. The apparatus according to claim 1, wherein the exit face is covered by a transparent cover plate.

11. The apparatus according to claim 1, wherein the light source comprises a first light emitter that outputs first light having a first wavelength and a second light emitter that outputs second light having a second wavelength.

12. The apparatus according to claim 11, wherein the first light having the first wavelength is focused to a first focal plane, and wherein the second light having the second wavelength is focused to a second focal plane that is different from the first focal plane.

13. The apparatus according to claim 12, wherein the first light is to be focused to the first focal plane concurrent to the second light being focused to the second focal plane, and wherein first focal plane ranges associated with the first light are measured concurrent to second focal plane ranges associated with the second light.

14. The apparatus according to claim 1, further comprising a focus shifting mechanism for shifting a focal plane of the optics system.

15. The apparatus according to claim 14, wherein the focus shifting mechanism is configured to shift one or more lenses of the optics system along the optical axis.

16. The apparatus according to claim 1, wherein the outermost marginal ray of the light with respect to the optical axis of the optics system is at a first angle with the outermost chief ray that is complementary to a second angle defined by the outermost chief ray with the optical axis, wherein the outermost chief ray is an outermost off-axis chief ray.

17. The apparatus according to claim 16, wherein the outermost marginal ray of the light with respect to the optical axis of the optics system is at a first angle with the outermost off-axis chief ray that is complementary to a second angle defined by the outermost off-axis chief ray with respect to the optical axis.

18. An apparatus for confocal imaging, the apparatus comprising:
    a light source for generating light;
    an optics system for focusing the light; and
    a light-guiding part having an entrance face and an exit face,
    wherein the light source, the optics system and the light-guiding part are arranged such that chief rays of the light before entering the light guiding part are divergent to each other, and
    wherein an off-axis chief ray of the light diverges at a divergence angle with respect to an optical axis and an outer marginal ray of the light converges at an angle with respect to the off-axis chief ray that is complementary to the divergence angle.

19. The apparatus according to claim 18, wherein the light source comprises a first light emitter that outputs first light having a first wavelength and a second light emitter that outputs second light having a second wavelength.

20. The apparatus according to claim 19, wherein the first light having the first wavelength is to be focused to a first focal plane, wherein the second light having the second wavelength is to be concurrently focused to a second focal plane that is different from the first focal plane, and wherein first focal plane ranges associated with the first light are measured concurrent to second focal plane ranges associated with the second light.

* * * * *